United States Patent
Osorio

(10) Patent No.: US 8,951,192 B2
(45) Date of Patent: Feb. 10, 2015

(54) SYSTEMS APPROACH TO DISEASE STATE AND HEALTH ASSESSMENT

(75) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 702 days.

(21) Appl. No.: 12/816,357

(22) Filed: Jun. 15, 2010

(65) Prior Publication Data

US 2011/0306846 A1 Dec. 15, 2011

(51) Int. Cl.
*G06F 19/00* (2011.01)
*A61B 5/00* (2006.01)

(52) U.S. Cl.
CPC ............ *A61B 5/4094* (2013.01); *A61B 5/4842* (2013.01); *A61B 5/7275* (2013.01); *G06F 19/3431* (2013.01); *G06F 19/3418* (2013.01); *G06F 19/3443* (2013.01); *G06F 19/345* (2013.01)
USPC .......................................... 600/301; 600/300

(58) Field of Classification Search
None
See application file for complete search history.

(56) References Cited

U.S. PATENT DOCUMENTS

| | | | |
|---|---|---|---|
| 6,440,066 B1 * | 8/2002 | Bardy | 600/300 |
| 7,107,253 B1 * | 9/2006 | Sumner et al. | 706/45 |
| 2004/0230105 A1 * | 11/2004 | Geva et al. | 600/301 |
| 2005/0060007 A1 * | 3/2005 | Goetz | 607/48 |
| 2006/0094972 A1 * | 5/2006 | Drew | 600/523 |
| 2006/0224191 A1 * | 10/2006 | Dilorenzo | 607/3 |
| 2007/0255118 A1 * | 11/2007 | Miesel et al. | 600/300 |
| 2007/0265508 A1 * | 11/2007 | Sheikhzadeh-Nadjar et al. | 600/300 |
| 2007/0265677 A1 * | 11/2007 | Giftakis et al. | 607/45 |
| 2007/0276439 A1 * | 11/2007 | Miesel et al. | 607/2 |
| 2008/0119900 A1 * | 5/2008 | DiLorenzo | 607/3 |
| 2009/0292180 A1 * | 11/2009 | Mirow | 600/301 |
| 2009/0292478 A1 * | 11/2009 | Avinash et al. | 702/19 |

OTHER PUBLICATIONS

Chilton, et al., "Cardiovascular Comorbidities of Type 2 Diabetes Mellitus: Defining the Potential of Glucagonlike peptide—1-Based Therapies" *Am. J Med.* (2011) 124, S35-S53.
Guh, et al., "The incidence of co-morbidities related to obesity and overweight: A systematic review and meta-analysis" *BMC Public Health* 2009;9:88.
Lang, et al., "Non-cardiac comorbidities in chronic heart failure" *Heart* 2007;93:665-671.
Marcangelo, et al., "Psychiatric Aspects of Epilepsy" *Psychiatr Clin N Am* 30 (2007) 781-802.
Nicolai, et al., "Cognitive and behavioral effects of nocturnal epileptiform discharges in children with benign childhood epilepsy with centrotemporal spikes" *Epilepsy & Behavior* 8 (2006) 56-70.

(Continued)

*Primary Examiner* — William Thomson
*Assistant Examiner* — Davin Sands

(57) ABSTRACT

Methods, systems, and apparatus for assessing a state of an epilepsy disease or a comorbidity thereof are provided. The methods comprise receiving at least one autonomic index, neurologic index, stress marker index, psychiatric index, endocrine index, adverse effect of therapy index, physical fitness index, or quality of life index of a patient; comparing the at least one index to at least one reference value; and assessing a state of an epilepsy disease or a body system of the patient based on the comparison. A computer readable program storage device encoded with instructions that, when executed by a computer, perform the method described above is also provided. A medical device system capable of implementing the method described above is also provided.

24 Claims, 19 Drawing Sheets

(56) References Cited

OTHER PUBLICATIONS

Rabec, et al., "Respiratory Complications of Obesity" *Arch. Bronconeumol.* 2011;47(5):252-261.

Sevcencu, et al., "Autonomic alterations and cardiac changes in epilepsy" *Epilepsia* 51(5):725-737, 2010.

Strazullo, et al., "Excess Body Weight and Incidence of Stroke : Meta-Analysis of Prospective Studies With 2 Million Participants" *Stroke* 2010; 41:e418-e426.

Tellez-Zenteno, et al., "Psychiatric comorbidity in epilepsy: A population-based analysis" *Epilepsia* 48(12):2336-2344, 2007.

Tomson, et al., "Medical risks in epilepsy: a review with focus on physical injuries, mortality, traffic accidents and their prevention" *Epilepsy Research* 60 (2004) 1-16.

Tomson, et al., "Sudden Unexpected Death in Epilepsy: A Review of Incidence and Risk Factors" *Epilepsia* 46(Suppl. 11):54-61, 2005.

Zaccara, "Neurological comorbidity and epilepsy: implications for treatment" *Acta Neurol Scand* 2009: 120: 1-15.

\* cited by examiner

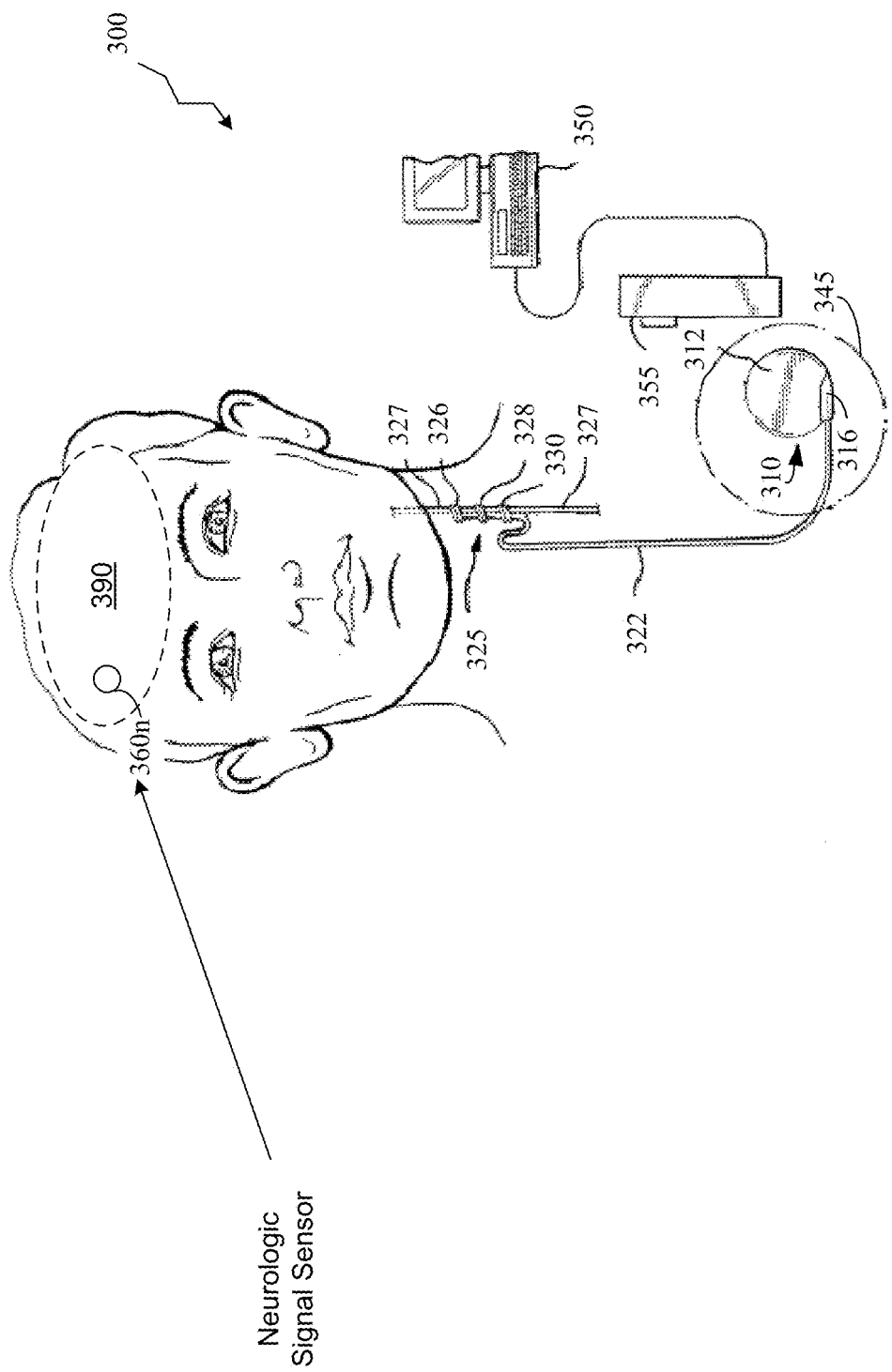

SYSTEMS APPROACH TO DISEASE STATE AND HEALTH ASSESSMENT

This application is related to an application filed concurrently herewith, entitled "A Systems Approach to Comorbidity Assessment," having the same inventor, the disclosure of which is hereby incorporated herein by reference.

FIELD OF THE INVENTION

This invention relates generally to medical device systems and, more particularly, to medical device systems and methods capable of assessing a state of a disease.

DESCRIPTION OF THE RELATED ART

Diseases or disorders and their treatments, if available, often have a deleterious impact on the patient's overall health and well being. Traditionally, medical practice focuses its diagnostic and therapeutic efforts to the specific disorder (primary diagnosis), an approach that while necessary and, in at least certain ways, useful, ignores the "spill-over" effect of the disease or treatment on the patient's overall health and well being. By compartmentalizing diseases, a reductionist practice, medicine as presently practiced ignores the substantial and fundamental loss of information inherent to this approach. That is, fragmenting into its constituents parts complex, non-linear network systems (of which the human body is a paradigm) so as to facilitate their study. This fragmentation will often lead to imprecise and distorted findings because the assembly of systems (which determines overall health) is greater than the sum of its parts. This viewpoint central to general systems theory applies to various embodiments of the present invention. For example, embodiments disclosed herein illustrate how the deleterious impact on the patient as a whole is a function of the disease type, its rate of progression, severity, and duration, and of the type of therapy and its dose. Clearly, the impact is often more severe or complicated when the patient has multiple disease types or several therapies.

Various elements of the system interact through interconnected feed-back and feed-forward loops. FIG. 16, for example, illustrates the complex nature of the primary disease of obesity where feed-forward and feed-back loops can accelerate the progression of the disease. FIG. 17 provides a similar example for the primary disease of epilepsy. Embodiments of the present invention utilize systems theory's tenets by recognizing and incorporating a primary disease or disorder with its co-morbidities. Numerous embodiments of the present invention demonstrate how largely positive feed-forward and feed-back loops between diseases or disorders and their expected mutually amplifying effects result in wide variations of disease/disorder progression or regression. Further, the potential for transmutability and context-dependency of whether a disorder or disease is a primary one or a co-morbidity is apparent through the example of how obesity may become a co-morbidity in subjects treated for epilepsy.

Obesity and its co-morbidities together provide a non-limiting example that illustrates how undesired "spillover" effects from a primary disease or condition under consideration can negatively impact the patient's health. Obesity is a disorder of epidemic proportions in the US, and substantially increases the patient's risk of developing diabetes mellitus, arterial hypertension, hyperlipidemia and obstructive sleep apnea, while shortening life span and degrading quality of life. Arterial hypertension, diabetes and hyperlipidemia, in turn, accelerate atherosclerosis, which further increases the risks for myocardial infarction, stroke, congestive heart failure, and avascular gangrene. Similarly, obstructive sleep apnea causes intractable arterial hypertension, atrial fibrillation, cognitive deterioration, depression, sexual dysfunction, and chronic headaches.

This exemplary list of a primary disorder (e.g., obesity, FIG. 16) and its "co-morbidities" illustrates how the human body may be considered as a densely interconnected (bidirectional) network of "nodes" (body systems and/or organs), stressing the dependence of its complex dynamics on the integrity of each of its component "nodes". The interactions among the nodes may be viewed as feed-forward or feedback loops, that under pathological conditions have an amplifying effect or "positive" (e.g., positive feedback) effect on themselves and on the network. A "systems" approach to human disease which would acknowledge the anatomical and functional interconnections one organ or body system's function has on the others, is lacking in the field of health care, to the detriment of quality of care and cost-effectiveness. Such a "systems" approach, exemplified by embodiments of the present invention, provides for the systematic and reproducible means of automatically tracking the evolution of the primary disease or disorder (e.g., obesity) and of its co-morbidities (e.g., hypertension, diabetes, sleep apnea, etc.) to identify or preferably anticipate their contribution to any change in the patient's overall health. Embodiments of the invention may be used either to prevent the emergence of co-morbidities, to ameliorate their deleterious impact, and/or to improve or stabilize them. As a result, it is possible to improve or preserve health and quality of life of the patient while lessening the upwardly spiraling costs of health care.

While many diseases, their co-morbidities, or side effects of treatment may negatively affect the general health and well-being of a patient, only a handful of other examples will be furnished herein. Such examples should not be construed as limiting the scope of invention but, on the contrary, merely to serve as examples underscoring the widespread applicability and usefulness of the invention.

Epilepsy affects approximately 60 million people worldwide of whom roughly 23 million are resistant to multiple medications. Pharmaco-resistant seizures are associated with an increase in mortality and morbidity rates (compared to the general population and to epileptics whose seizures are controlled by medications) eventual impairment of cognitive functions and mental health and with markedly degraded quality of life for patients and their families. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing. In the USA alone, the annual cost of epilepsy care is over USD 15 billion (in 1995 dollars), most of which is attributable to subjects with pharmaco-resistant seizures. Certain pharmacological agents used for treatment of epilepsy cause osteoporosis, reproductive dysfunction, liver, bone marrow, kidney, and skin damage, neurologic and psychiatric dysfunction, weight gain and in rare cases, death. Various epilepsy therapies, such as thermal manipulation of epileptogenic tissue or local/direct delivery of drugs to it, may also cause adverse effects, such as neurologic, autonomic, psychiatric, sleep, appetite, sex drive, and other disturbances.

Diabetes mellitus, a highly prevalent disease, causes autonomic dysfunction, accelerates atherosclerosis and with it the incidence of heart attacks, strokes and avascular gangrene and has a negative impact on quality of life and mental health. In patients with juvenile or Type I diabetes, the physiological responses to counteract hypoglycemia (a common adverse effect of insulin) become blunted or absent making this serious condition asymptomatic. That is, the symptoms that make a person aware that blood sugar is low—and which motivate or compel the person to eat—do not occur in these patients, considerably increasing the risks of brain damage and death due to hypoglycemia.

Parkinson's is a disease of the brain's basal ganglia, whose main function is modulation of posture and movements. Parkinson's is associated with autonomic dysfunction and increased risks of injury, dementia, and head and bodily injuries caused by falls. Autonomic dysfunction, in turn, increases the risk of cardiac arrhythmias, syncope, and death, with falls enhancing this risk. These selected examples underscore the importance of developing and implementing what is referred herein as a systems approach to diseases, where the disease in question and its impact on the other body organs and functions (co-morbidities), are assessed as a function of time and space-state and this information is used for early intervention so as to prevent deterioration and further disabilities.

Co-morbidities are common with many other disorders or diseases, further imposing psycho-social and/or financial burdens on the patient, the patient's family, and society in general, and worsening quality of life. Other costly and highly burdensome diseases or disorders include cardiovascular disorders (such as congestive heart failure and atrial fibrillation), respiratory disorders such as chronic obstructive pulmonary disease, depression and other mood disorders, schizophrenia, anxiety disorders and other neuropsychiatric disorders, neuro-degenerative diseases such as Alzheimer's, traumatic brain injury, migraine headache, eating disorders (such as obesity, anorexia nervosa, and bulimia), sleep disorders, hypertension, and pain (including neuropathic pain and fibromyalgia).

Regardless of the disease in question, it would be useful to assess the evolution of the patient's primary disease and comorbidities through characterization of their direction (progression, regression, or stabilization), magnitude, and rate of change and comorbidities, since disease progression is usually correlated with emergence of new or worsening of existing comorbidities, further degrading the patient's health and well-being. For example, certain types and severities of epilepsy are associated with changes (compared to the general population) in the occurrence of sudden unexpected death (SUDEP), serious accidents, or other fatal events, such as suicide. It would be useful to assess the clinical evolution of a patient's epilepsy and its co-morbidities to determine the type(s) of risk(s) and their probability of occurrence to either revert the trend, if possible, and if not, to institute measures to minimize and manage those risks. No automated system for making this assessment, determination, and risk management is known to this inventor at this time.

Although treatment options for many diseases exist, the efficacy of a particular treatment option for a particular disease in a particular patient may be unpredictable. Further, the efficacy of a particular treatment option for a particular disease in a particular patient may be difficult to gauge, and further, such gauging may be subjectively determined by the patient, the physician, or a combination thereof. Also, a particular treatment option for a particular disease in a particular patient may lead to various side effects, some of which may be difficult to gauge.

It would be desirable to have methods and apparatus to reproducibly and in a clinically useful and cost-effective manner: a) assess a state of a disease of a patient, such as a disease that impacts, directly or indirectly, a neurological, autonomic, endocrinologic, or psychiatric disease and extent to which they impair overall health and well being via the emergence of "co-morbidities"; b) assess the therapies' side effects; c) improve or stabilize a existing disease and prevent the emergence of co-morbidities; d) prevent or ameliorate adverse treatment effects. The direct clinical and psychosocial benefits to patients and the ensuing decrease in the financial burden to the health care system and society of successfully implementing said automated comprehensive assessment are readily apparent. The state of the art lacks an efficient, systematic, and user-friendly automated system for making this assessment. Desirably, an apparatus used in assessment would be implantable or portable and operate in real-time or off-line. It would also be desirable for such an apparatus to incorporate and analyze, for purposes of assessing disease state, data obtained using other diagnostic devices including those that are not portable, implantable, or implementable into hardware or software. The assessment may be made by an apparatus automatically and this either contingently (e.g., triggered by a large or sudden change in an index, or by a patient's or caregiver command) or at predetermined times; the assessment may be also made based on clinical judgment. The assessment may be quantitative (magnitude and rate), semiquantitative (questionnaires, subjective scales), or qualititative (e.g. small, slow, etc).

SUMMARY OF THE INVENTION

In one embodiment, the present invention provides a method for assessing an epilepsy disease state. In one embodiment, the method comprises receiving at least one autonomic index; receiving at least one neurologic index; comparing the at least one autonomic index to at least a first reference value associated with the at least one autonomic index; comparing the at least one neurologic index to at least a second reference value associated with the at least one neurologic index; assessing a state of an epilepsy disease of a patient based on the comparing; and providing an output relating to the assessment, the output comprising at least one of disease stability, disease progression, disease regression, or a finding that a disease state cannot be determined.

In one embodiment, the present invention provides a method for assessing a patient's health. In one embodiment, the method comprises receiving at least one assessment of at least one of a patient's epilepsy disease state, a quality of life, or a physical fitness; comparing the at least one assessment to at least one reference value associated with at least one previous assessment from the patient or with normative data; assessing at least one of the patient's epilepsy disease state, quality of life, or physical fitness based on the comparing; and providing an output relating to an assessment of the patient's health, wherein the output comprises at least one of a disease state stability, disease state progression, disease state regression, a finding that the disease state cannot be determined, quality of life stability, quality of life improvement, quality of life decline, a finding that the quality of life cannot be determined, physical fitness stability, physical fitness improvement, physical fitness decline, or a finding that physical fitness cannot be determined.

In one embodiment, the present invention provides a method for assessing a comorbidity associated with epilepsy. In one embodiment, the method comprises receiving at least one of an autonomic index, a neurologic index, or both; comparing the at least one index to at least one reference value associated with the at least one index; assessing a state of a body system of the patient based on the comparing, wherein the body system comprises at least one of an autonomic system, a neurologic system, a psychiatric system, an endocrine system or subsystems of the foregoing; and providing an output relating to the assessment, wherein the output comprises at least one of body system stability, body system improvement, body system decline, or a finding that a state of the body system cannot be determined, wherein the body system is a site of the comorbidity.

In one embodiment, the present invention provides a computer readable program storage medium encoded with instructions that, when executed by a computer, perform a method as described above.

BRIEF DESCRIPTION OF THE DRAWINGS

The invention may be understood by reference to the following description taken in conjunction with the accompanying drawings, in which like reference numerals identify like elements, and in which:

FIG. 3C provides a stylized diagram of a medical device implanted into a patient's body, in accordance with one illustrative embodiment of the present invention;

Figure 1:
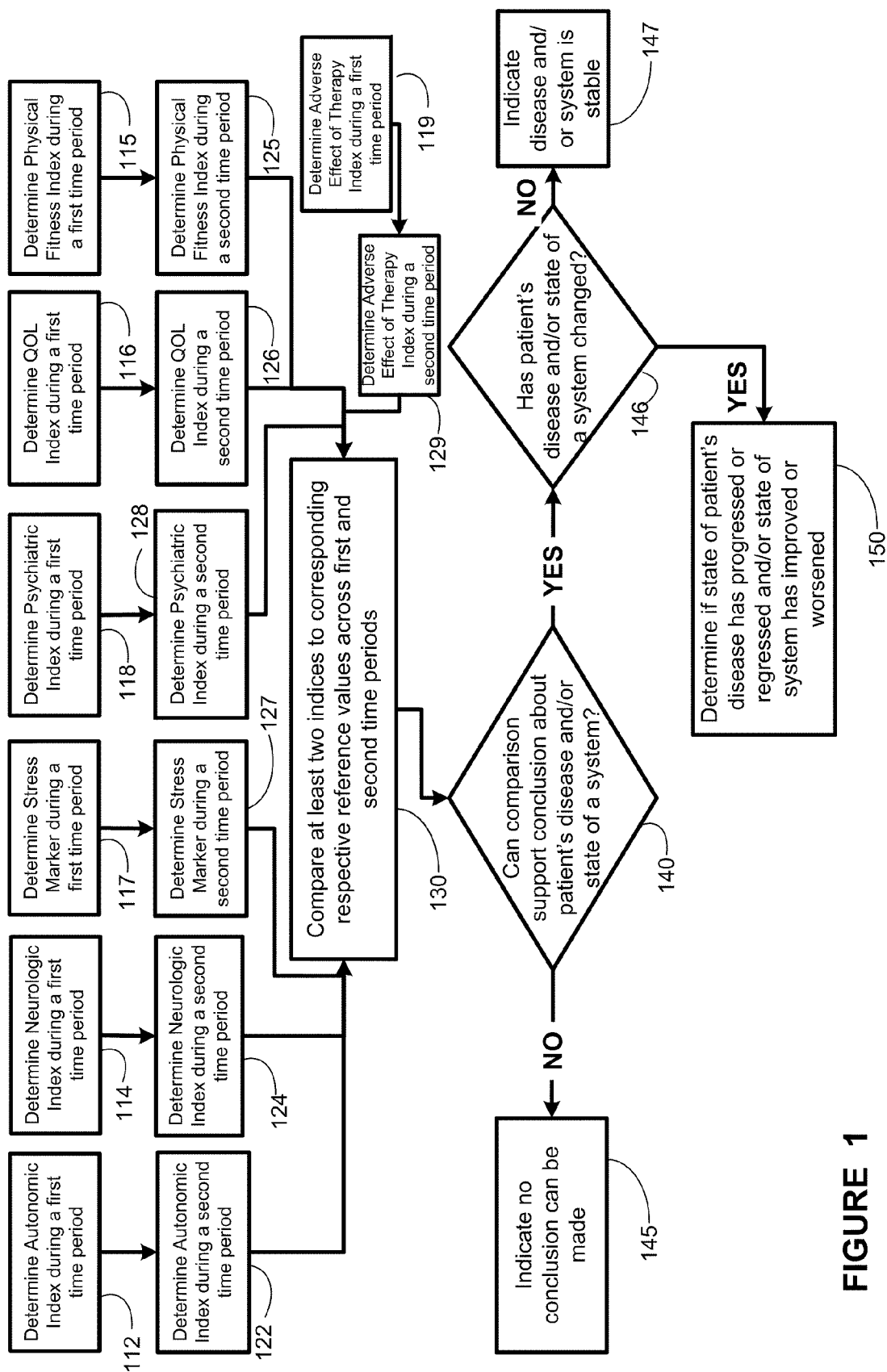
FIG. 1 illustrates a flowchart depiction of a method for assessing a state of a patient's disease, in accordance with an illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering a therapeutic signal generated by an IMD to a tissue), sensing electrodes (i.e., electrodes for sensing a physiological indication of a patient's body), and/or electrodes that are capable of delivering a therapeutic signal, as well as performing a sensing function.

This invention makes uni-variate (e.g., neurological index only) or multivariate (e.g., neurological, autonomic, psychiatric, etc.) comparisons of the effects of the patient's disease state (and, in some embodiments, a treatment for the patient's disease) on one or more body systems. Comparisons may include one or more index parameters associated with body systems. Index parameters may involve measures of central tendency, measures of dimensionality including fractal dimensionality, measures of non-linearity, measures of non-stationarity, measures of long-range dependence or correlation, and measures of clustering, such as the pseudo F statistic, including size, shape number and distance between clusters. The index parameters may also comprise distributions of any of the foregoing measures.

The index measures may be treated separately or as a composite (i.e., a single measure of multivariate indices). Where a composite measure is used, the component indices may be weighted differently based on its impact on subject's well-being or safety, and may be derived from indices obtained from either implanted or external devices, or from historical data.

Comparisons may be intra-subject or inter-subject, including to tables of normative values from healthy or special populations, and may be performed as a function of time or state space. Comparisons may be quantitative and associated with a statistical significance value or qualitative or based on clinical judgment. The analyses performed as part of embodiments of this invention will yield four quantitative or qualitative outcomes: disease progression (deterioration in the index) expressed as one of a numerical difference in relation to past values, a rate of change of the index as a function of time from the previous measurements, or a qualitative change (e.g., minimal and slow or marked and rapid); disease stabilization (no change in the index); disease regression (improvement in the index); or insufficient information/undecidable. The outcomes will be automatically time-stamped, reported and stored for comparisons with past and future measurements, along with the index values and comparison results leading to the quantitative, semi-quantitative or qualitative outcome reported for the index. Models of disease state may be built to issue forecasts or prognoses of the patient's future condition or disease state, using tools or methods (e.g., Kalman filtering, Bayesian statistics, etc.) known to the person of ordinary skill in the art. Changes in index values relative to past or normative data may also be used to stratify patients into risk categories. Automated warnings may be issued for either large or rapid deterioration (indicative of disease progression) in any of the index value at the time it is observed or detected or forecast so that treatment or preventive measures may be instituted.

Embodiments of the present invention provide for assessing a state of a disease of a patient. In some embodiments, one or more of an autonomic index, a neurologic index, a stress marker index, a psychiatric index, an endocrine index, an adverse effect of therapy index, a physical fitness index, and/or a quality of life index may be compared to predetermined or corresponding reference values. The assessment of the disease may be performed based upon the comparisons of the indices to respective reference values.

Any disease may be considered herein. As discussed above, it should be apparent that various diseases may coexist in a positive feedback loop. The term "primary disease" may be used herein to refer to a disease which is the subject of medical attention. For example, for a patient having both epilepsy and congestive heart failure, a neurologist may consider epilepsy a primary disease and congestive heart failure a secondary disease or comorbidity; whereas a cardiologist may consider the opposite.

As should be apparent, the methods and systems of the present invention may be applied in situations where one or more diseases are the subject of medical attention. For example, the methods of the present invention may be used by a patient suffering from epilepsy to monitor the state of this disease and any comorbidities associated with it. For another example, the methods of the present invention may be used by a patient suffering from both epilepsy and diabetes mellitus to monitor the state of each disease and any comorbidities associated with either disease. As will be apparent to the person of ordinary skill in the art having the benefit of the present disclosure, the states of any one or more known diseases, including but not limited to the exemplary ones referred to above, and their associated comorbidities may be monitored.

As will be described in further details below, FIG. 1 shows one exemplary embodiment of a method according to the present invention. One or more of an autonomic index, a neurologic index, a stress marker index, a psychiatric index, an endocrine index, an adverse effect of therapy index, a physical fitness index, and/or a quality of life (QOL) index are determined during a first time period at steps 112, 114, 115, 116, 117, and/or 119. Similarly, one or more of an autonomic index, a neurologic index, a stress marker index, a psychiatric index, an endocrine index, an adverse effect of therapy index, a physical fitness index, and/or a quality of life (QOL) index are determined during a second time period at steps 122, 124, 125, 126, 127, 128, and/or 129. Thereafter, at least two indices are compared to respective reference values across the first and second time periods at step 130.

In addition to time, "space states" can be used to define conditions in which the index values are determined Herein, "space states" refer to index values as measured at different locations in or on the patient's body, or in the same location but during different states (e.g, wakefulness vs. sleep; sedentary or resting conditions vs. exercise). For example, the patient's oxygen saturation can be measured by a pulse ox device, such as fingertip-mountable oxygen saturation sensor, and simultaneously the patient's heart rate can be measured by an appropriate device, such as an implantable medical device. For another example, the patient's oxygen saturation can be measured during a resting condition and during physical exertion. An index can comprise data from one or more locations in or on the body collected at one or more times.

Assessments of disease state or comorbidity based on tests, scales, or questionnaires may be administered automatically on-line or off-line. Adaptation and validation of said tests, scales or questionnaires may be performed as needed to ensure reproducibility and proper interpretation.

Once the comparison is made, a determination 140 is made whether the comparison can support the conclusion that the patient's disease and/or a state of a body system of the patient has changed or remained stable. If not, an indication 145 is made that no conclusion about the patient's disease and/or a body system of the patient can be made.

Optionally, the indication 145 of no conclusion can further comprise reporting one or more reasons for the indication; e.g., the sample size is too small, the data is too noisy, or the analysis is too complex to be performed.

If the comparison can support the conclusion that the patient's disease and/or a state of a body system of the patient has changed or remained stable, a determination 146 is made whether the patient's disease and/or a state of a body system of the patient has changed. If it has not, an indication 147 is made that the patient's disease and/or a body system of the patient is stable.

However, if the comparison indicates the patient's disease and/or a state of a body system of the patient has changed, then a determination 150 is made whether the patient's disease has progressed or regressed relative to a previous assessment and/or whether the patient's body system has improved or worsened relative to a previous assessment.

Figure 2:
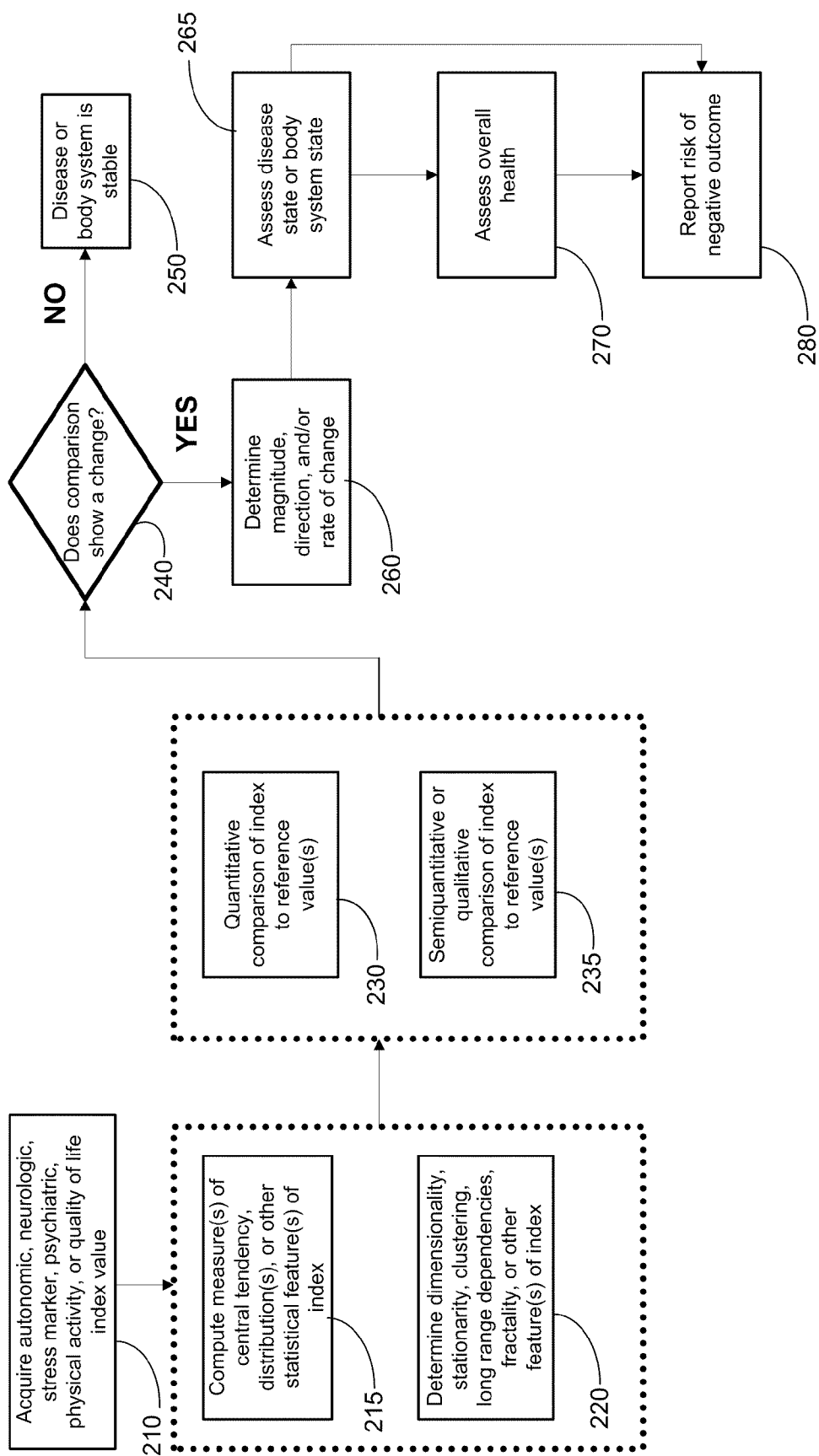
FIG. 2 illustrates a flowchart depiction of a method for assessing a state of a patient's disease, in accordance with an illustrative embodiment of the present invention.

As will be described in further details below, FIG. 2 shows another embodiment of a method according to the present invention. In this embodiment, one or more index values are acquired 210, and values derived from measure(s) of central tendency are computed 215 and/or other features (e.g., dimensionality, stationarity, clustering, long range dependencies, fractality, etc.) are determined 220. Thereafter, the features are compared to a reference value, in a quantitative manner 230 (such as statistically or non-statistically) and/or a semi-quantitative or qualitative (e.g., reflective of clinical judgment) manner 235.

A determination 240 is then made as to whether the comparison shows a change. If the determination is "no," the disease or body system is considered stable (box 250). If the determination is "yes," the magnitude, direction, and/or rate of change is determined 260, from which the state of the disease or body system can be assessed 265. If desired, the patient's overall health may be assessed 270, in light of the disease state, body system state, and/or other parameters. Alternatively or in addition, a risk of a negative outcome, such as risk of death, disease progression, new comorbidity, or the like can be reported 280.

From the comparisons, parametric or non-parametric statistical tests may be applied to measures of central tendency or to distributions thereof. Such tests include, but are not limited to, Student's t-test, Fisher's test, ANOVA, the Kolmogorov-Smirnoff, or the Mahalanobis, among others. If the measure(s) of central tendency or the distribution(s) are statistically significantly different, the magnitude and direction of the deviation may be estimated using appropriate tests or measures. Additionally or alternatively, clinical judgment may be applied to determine if the changes (whether or not statistically significant) are worthy of attention and merit intervention. Analyses may be performed on the mean, median, standard deviation, coefficient of variation, nth percentile, or any other measure of central tendency of a statistical distribution of index values. Analyses may be performed, when applicable, using spectral analysis, high order spectral analysis, detrended fluctuation analysis, fractal analysis, multifractal analysis, correlation dimension, and combinations thereof. Other techniques, such as regression analyses, eigen methods (e.g. principal component and canonical correlation analysis), co-variance analyses, bootstrapping, or Monte Carlo may be also used, among others known to the person of ordinary skill in the art.

Generally, biological data is non-stationary (the statistical properties change as function of time) and has long-range dependence (the values or characteristics of the present datum depend on previous data values). A variable or observable is considered "stationary" if all of its statistical parameters are independent of time. Most statistical techniques are well suited for data that is stationary, but certain variables or observables (e.g. heart rate and heart rate variability) that can be used in this invention to assess disease state, are to some degree nonstationary or cyclo-stationary. The "identically distributed" assumption is violated when the sampled process is non-stationary, which, for example, can cause the sample mean to be under- or over-estimated.

A two prong approach can be used to maximize the information content extracted from the analyses and of non-stationary data to better assess disease state: 1. Minimization of non-stationarity and of long-range dependencies to obtain information devoid of certain external influences or perturbations that best reflect the body system's "static" behavior; 2. Utilization of methods that address non-stationarity and long-range dependence to gain insight into the body system's behavior under external influences. Approaches to manage or minimize non-stationarity (e.g., stratification) so that the data may be analyzed using conventional statistics are well known to those skilled in the art and can be applied to extract valuable insights into disease state.

Certain data (e.g., EKG, EEG) used in this invention to assess disease state have "memory" which manifests as long range dependences. That is, values are not independent from each other such that present values are influenced by past ones. Estimation of the Hurst exponent and Detrended Fluctuation analysis may be used, among other methods, to characterize these type of data.

On the assumption a healthy subject's body is continually responding to changes in the environment, changes in the degree of non-stationarity and in long-range dependence in a biological time series, especially decreases in non-stationarity and/or long-range dependence, are usually indicative of dysfunction.

Time-frequency methods may be also applied to the analyses and processing (including detection, estimation, filtering, etc) of nonstationary processes that are some of the subject matter of this invention. The methods include but are not limited to the time-frequency autoregressive moving-average (TFARMA) model, as well as its special cases, the TFAR and TFMA models as they are computationally efficient and stable, retaining the simplicity and intuitiveness of the power spectral density. The coherent and incoherent statistics based in the sample coherence statistic (that apply a measure of fitness) and other methods based on the theory of periodically correlated (cycloperiodic) processes are particularly useful for analyses of biological data (e.g., heart rate variability, cortisol levels) subject to circadian variations.

Other methods that can be used include the heterogeneous autoregressive (HAR) models, the autoregressive moving average process of order (p,q) (ARMA(p,q) process), the autoregressive integrated moving average process of order (p,d,q) (ARIMA (p,d,q), the autoregressive fractionally integrated moving average process (ARFIMA(p,d,q) process), and the vector fractionally integrated autoregressive moving-average (VARFIMA) model.

The smooth localized complex exponentials (SLEX) model may be also applied and the best model can be selected using the penalized log energy criterion, which may be derived to be the Kullback-Leibler distance between a model and the SLEX principal components of the multivariate time series.

Certain data (e.g., EKG, EEG) used in this invention to assess disease state have "memory" which manifests as long range dependences. Estimation of the Hurst exponent and Detrended Fluctuation analysis may be used, among other methods, to characterize these type of data.

From this information, a prognosis formulated on the degree and rate of, e.g., cognitive changes is determined 260, the prognosis or a calculated probability of a serious outcome (e.g. mortality or extreme morbidity) 265, and/or a probability of an accident or injury 270, are estimated and provided to a predesignated person(s) so that appropriate and timely action(s), including preventive ones, may be taken. Models may built to simulate the temporal evolution of the various indices and, using these models, the probability estimates of various outcomes may be optimized.

In one embodiment, the present invention provides a method, apparatus and system to perform assessment of a state of a primary disease and/or co-morbidities of a patient and use these data to assess the patient's state of health and well-being. Embodiments disclosed herein call for receiving at least one first autonomic index, neurologic index, stress marker index, psychiatric index, an endocrine index, a physical fitness index, or quality of life index of a patient. The embodiments disclosed herein may also comprise receiving at least one second autonomic index, neurologic index, stress marker index, psychiatric index, endocrine index, physical fitness index, or quality of life index of the patient.

As used herein, the term "signals" includes (i) the "raw" signal (e.g., EKG) as recorded with a device, or parts or components of said signal (e.g., R-wave peaks), (ii) features derived from the "raw" signal using statistical, mathematical, or spectral tools (e.g., heart rate variability derived from R wave intervals, heart rate variability triangular index, SDNN, pNN50, LF, HF, LF/HF, etc.), (iii) the relationship the signal has with other signals or events, such as changes in heart rate as a function of respiratory frequency and/or tidal volume; and (iv) any recordable output such as cognitive functions, electrical, chemical, mechanical, thermal, or acoustic signals or any other information that may be used on any time scale to infer or extract useful information, about the state of a subject or of any of his organs. The signals may be analog or digital and can be converted therebetween as a routine matter for the person of ordinary skill in the art having the benefit of the present disclosure.

For example, in the case of EKG, this signal can be compared to itself (e.g., compiling a master EKG signal by combining parallel EKG signals detected from electrodes), compared to another body signal (e.g., aligning R waves of the EKG to respiration patterns or EEG patterns), or compared to events or non-body signals (e.g., EKG variations due to circadian rhythms, stress, exercise, or emotions). Similarly, other body signals discussed herein contain a myriad of information packed into the signal. The term "signal" is used herein to include all of this additional information that can be extracted or inferred from the signal and not simply the raw signal alone.

In another embodiment, one or more windows vary in window length as a function of time, disease state, another variable, or parameter.

In one embodiment, three or more windows are used to allow the comparison of isolated periodic events in the patient's life. For example, the system can compare indices by stratifying data and comparing one night to previous night(s) or designated times (e.g, 12:00 AM-06:00 AM, to the same time interval. Similarly, the system can compare day to previous day(s), REM sleep to prior REM sleep, morning to prior morning(s), cardiovascular exercise to previous cardiovascular exercise session(s), etc. as a function of ultradian, circadian, "lunar" or other rhythms. Comparisons may be made as a function of ultradian, circadian, "lunar" or other rhythms and between similar strata or different strata.

In one embodiment, the first index has two or more windows of different lengths associated with it. The second index can have just one window, or it can also have two, three, or more windows associated with it. Monitoring the entropy of the HRV signal, for example, could track the entropy in a 30 second window, a 24 hour window, and a 6 month window.

In one embodiment, the first index is a first autonomic index and the second index is a second autonomic index. In a further embodiment, the first autonomic index is a cardiovascular index or a respiratory index, and the second autonomic index is a cardiovascular index or a respiratory index.

In one embodiment, the first index is an autonomic index and the second index is a neurologic index. Exemplary autonomic indices include, but are not limited to, those derivable from cardiovascular signals, breathing signals, pupillary signals, skin signals, or blood pressure, among others. In one particular embodiment, the autonomic index is heart rate, values calculable from heart rate (such as magnitude and/or rate of change of heart rate, and heart rate variability, among others), heart beat wave morphology, and heart beat complex morphology (including measures of premature ventricular contractions (PVCs)), among others. Signals relating to these particular indices can be detected by any appropriate sensor, such as an R-wave detector or an electrocardiography (EKG) device, among others.

The definition of various indices as autonomic or neurologic, or various autonomic indices as cardiovascular or respiratory, is to some extent arbitrary, though the present disclosure uses these terms in a consistent manner apparent to the person of ordinary skill in the art. Specifically, the autonomic system, which is under brain (neurological) control, exerts (in a normal body) powerful influences on the cardiovascular, respiratory, and gastrointestinal systems. The integrity of these body systems is a condition for optimal brain (neurological) function. For simplicity and clarity, the term "autonomic" system or index will encompass cardiovascular, respiratory, dermal (skin), pupillary, gastrointestinal systems or their indices.

Brain neurological signals may be derived from EEG, ECoG, magnetoencephalography, brain imaging methods and modalities, chemical methods, EMG, or accelerometry, among others. Body kinetic neurological signals can be detected by electromyography, accelerometry, and/or inclinometry, or means for measuring force, among others. Cognitive signals may be obtained via manual or automated tests and questionnaires.

Exemplary neurological indices include, but are not limited to, those derivable from electrical signals (EEG, evoked responses), chemical-metabolic signals, cognitive (relating to functional and cognitive decline, as well as risk of future decline) signals, and kinetic signals (relating to gait, posture, accessory movements, falls), hippocampus and entorhinal cortex volumes, basal forebrain nuclei volumes, and cortical thickness to determine the pattern and rate of atrophy. Other techniques, such as deformation-based and voxel-based morphometry, structural and effective connectivity by using diffusion tensor imaging, tractography, functional magnetic resonance imaging and positron emission tomography, may be employed to assess the state of disease. Other neurological signals (e.g. rate, amplitude and pattern of spikes) such as those generated by the cranial nerves spinal cord, spinal roots or nerves, may be used to assess disease state.

Through the application of appropriate techniques to EEG, ECoG, EKG, or other biological signals recorded from epileptic brains, maximal seizure intensity (Si), duration (Sd), and extent of spread (Sc) may be computed. These measures may be used to compute seizure severity (SS) by transforming them (Si, Sd, Sc) into their corresponding percentiles Pi, Pd, and Pc and calculating their average: $SS=(Pi+Pd+Pc)/3$. These measures (Si, Sd, Sc) may be used without transformation or they may be transformed using for example natural logarithms. Seizure severity and the time elapsed between seizures (interseizure interval) defined as the time between the end of a seizure and the onset of the next one provide insight into the status of a patient's epilepsy. For example, increases in mean or median seizure severity and/or decreases in mean or median interseizure interval would indicate the disease has progressed.

Cognitive neurological indices may comprise measures of attention, simple or complex reaction time, verbal or spatial memory, executive functions, calculation, language, reasoning, visuo-spatial functions, evoked responses, EEG, MEG, or brain imaging (e.g., static (MRI) or functional (e.g., PET or fMRI)) among others. In one embodiment, the neurologic index may include one of more tests such as, a structured clinical interview, Wechsler Adult Intelligence Scale (WAIS-III) but will be updating to WAIS-IV Wechsler Memory Scale-Third Edition (WMS-III: Logical Memory I & II, Faces I & II, Spatial Span), California Verbal Learning Test-$2^{nd}$ Edition (CVLT-II), Rey-Osterreith Complex Figure Test (ROCF), Continuous Visual Memory Test, Sentence Repetition Test (Multilingual Aphasia Examination), Complex Ideational Material (Boston Diagnostic Aphasia Examination), Category Fluency Test, Controlled Oral Word Association (COWA), Boston Naming Test (BNT), Wide Range Achievement Test-$4^{th}$ Edition (WRAT-IV: Reading), Trail Making Test (Part A & B), Wisconsin Card Sort Test (WCST), Ruff Figural Fluency Test (RFFT), Sensory Imperception Test, Finger-Tip Number Writing Test, Benton Facial Recognition Test, Grooved Pegboard Test, Finger Tapping Test, Thumb-Finger Sequencing Test, Edinburgh Handedness Inventory, Minnesota Multiphasic Personality Inventory-$2^{nd}$ Edition (If reading level$\geq 6^{th}$ grade; if not use Personality Assessment Inventory).

Responsiveness tests based on measurement of simple or complex reaction times, are the subject of copending patent application Ser. No. 12/756,065, filed Apr. 7, 2010, which is hereby incorporated by reference herein.

In one particular embodiment, the neurological index is a measure of responsiveness or a measure of physical (in)stability, such as number, frequency, or severity of falls. Signals relating to these particular indices can be detected by any appropriate sensor, such as an external responsiveness testing device or an internal responsiveness testing device (such as one making use of an implantable sound device to generate a tone or sound in proximity to the ear, an implantable accelerometer to detect a physical motion, such as the movement of a limb or a tap on the skin at the accelerometer implant site), among others.

Psychiatric indices (including, but not limited to, mood, thoughts, and hallucinations), and quality of life indices are also subject to measurement in the present invention. Those skilled in the art know of the existence of clinically validated tools to assess quality of life and psychiatric status. The measurements provided by these tools may be used to automatically warn the patient or the caregivers of impending psychiatric decompensation or of high risk of suicide, so that an adverse or fatal outcome may be averted through timely intervention.

In one embodiment, the quality of life (QOL) factors may include one or more of scales such as, but are not limited to: the generic scale for quality of life; the Psychological General Well-Being Scale (PGWB); the WHO-Five Well-Being Index (WHO-5); the Quality of Life in Depression Scale (QLDS); the Social Functioning Scale-36 (SF-36); the Social Functioning Scale-12 (SF-12); the Quality of Life Enjoyment and Satisfaction Questionnaire-Short Form (Q-LES-Q-SF); and the Streamlined Longitudinal Interval Continuation Evaluation-Condensed Version (SLICE-C).

Alternatively or in addition, the QOL index is a health-related QOL index indicative of the patient's morbidity or any co-morbidities.

Psychiatric assessment may entail administration of one or more of the following tests or scales: mini-mental state examination or Folstein test, abbreviated mental test score, Millon Clinical Multiaxial Inventory-III, psychometric tests such as the WISC or WAIS, Minnesota Multiphasic Personality Inventory, child Behavior Checklist, the Beck Depression Inventory. Other tests are the NEO-PI, the 16 PF, the OPQ (Occupational Personality Questionnaire), the Five Factor Personality Inventory-Children (FFPI-C.). which are based on the Big Five taxonomy. Additional tests include but are not limited to the Behaviour and Symptom Identification Scale (BASIS-32), the Beck Hopelessness Scale, the Bipolar Affective Disorder Dimension, the Scale Composite International Diagnostic Interview, the Depression-Anxiety stress scale, the General Health Questionnaire, the InterSePT Scale for Suicidal Thinking, the Kessler Psychological Distress scale, the Major (ICD-10) Depression Inventory Psychotic symptoms rating scale, the Psychological general well-being index, and the suicide intent scale.

Cardiovascular autonomic indices may be tested with the so called Ewing's battery, which consists of three tests reflecting cardiovascular parasympathetic and two tests reflecting cardiovascular sympathetic function: Heart rate response to forced breathing; heart rate response to the Valsalva maneuver; heart rate response to standing erect; blood pressure response to standing, and blood pressure response to handgrip. Other tests include baroreflex sensitivity, sympathetic skin response, heart rate and blood pressure variation during normal and deep breathing, maximum systolic blood pressure increase in isometric work, the Valsalva maneuver, or postural change, blood pressure response to postural changes including tilting, the 30:15 ratio of heart rate response to standing, and time domain parameters such as SDNN, PNN50, rMSDD, EKG morphology, EKG rhythm pattern, heart sounds, blood pressure, chest wall deflection, ejection fraction, heart size, ventricular wall thickness, and heart contractility, among others. These indices can be derived from signals detected by electrocardiography, blood pressure monitors, a microphone, apexcardiography, or echocardiography, among other techniques.

Respiratory autonomic signals, skin autonomic signals, temperature autonomic signals, and the like can be detected, and indices (e.g., rate, pattern, tidal volume, vital capacity, forced vital capacity, skin resistance, sweat production, tympanic temperature, rectal temperature, and core temperature, among others) derived therefrom, by techniques and apparatus known to the person of ordinary skill in the art.

Changes in catecholamines (e.g, epinephrine, serotonin) and in metabolites (vanillyl mandelic acid, metanephrine) in blood, urine, or other bodily fluids, during resting conditions or exercise, or as functions of time of day may be also be measured to assess the integrity of the autonomic nervous system. Direct recording of efferent postganglionic muscle sympathetic nerve traffic via microneurography and application of the regional norepinephrine spillover technique may be also used as autonomic indices. A technique using electrodes positioned on the abdominal skin to record stomach contractions (electrogastrography) provides information about autonomic function through measurement of the dominant frequency (power) of contractions and classify them as normal (eugastria) or abnormal (bradygastria, tachygastria).

Changes in hormone levels in blood or other bodily fluids, during resting conditions or exercise, or as functions of time of day may be also measured to assess the integrity of the endocrine system. For example, the human body has its highest melatonin levels between about midnight and eight a.m.;

variations in the time of highest melatonin levels, or increases or decreases in the levels themselves, may reflect impairment of the endocrine system.

Therapies may adversely impact any body system. The tests or measurements described above for assessment of autonomic, neurologic, psychiatric, or endocrine function described in multiple parts of this specification, may be used for identifying and quantifying adverse effects of any type of therapy for any disease. Assessment of liver, bone marrow, kidney, or skin may be performed with any of the existing blood (e.g liver enzymes, blood hemogram, creatinine, BUN, etc.), radiologic/imaging (liver or kidney ultrasound), or histologic (e.g. biopsies of bone marrow, skin, liver or kidney) tests that are common practice in medicine.

In this invention, "adverse effects of therapy" encompasses any and all body systems (e.g., neurological, autonomic, psychiatric, hepatic, renal, dermal, etc.) that may be negatively affected by any form of therapy (e.g., electrical, pharmacologic, thermal, cognitive, etc). It is remarked that autonomic and adverse effect of therapy indices share in common several dermal (skin) indices (e.g. temperature; color, texture), the only difference being that skin resistance is exclusively an autonomic index.

Changes in a person's physical fitness encompasses long-term and/or global measures of activity, such as measures of physical fitness (e.g., VO2max, etc.). Physical fitness may be defined as the capacity to carry out the day's activities, pursue recreational activities, and have the physical capability to handle emergency situations. Physical fitness can be measured using strength tests (e.g., One repetition max), speed and power tests (e.g., 30 m sprint; standing vertical jump), endurance Tests (e.g., Balke 15 minute run), and flexibility tests (e.g., sit and reach test).

In another embodiment, the index value may be derivable from one or more cranial nerve signals (e.g, spike frequency, amplitude, or pattern, among others). In yet another embodiment, the index value may be derivable from one or more autonomic nerve or ganglia signals (e.g, spike frequency, amplitude, or pattern, among others).

Seizures are powerful biological stressors and inductors of stress marker indices and deplete the body of certain antioxidants, such as glutathione peroxidase. Exemplary stress marker indices comprise changes (direction, rate, and magnitude) in glucose, prolactin, cortisol, catecholamines, chromogranin A, free radicals or reactive oxygen species, lactic acid, blood gases, N-acetylaspartate, in the expression of heat shock proteins, and in metabolites of any or all thereof. For example, a "cortisol parameter" refers to a stress marker index relating to cortisol or a metabolite thereof, and a "catecholamine parameter" refers to a stress marker index relating to a catecholamine or a metabolite thereof. The concentration of certain compounds that protect from biological stress (e.g., dehydroepiandrosterone or its sulfate conjugate, glutathione peroxidase) or the body's total antioxidant capacity may be also measured to determine if it is adequate and if not to increase it using commercially or naturally available antioxidants to stall disease progression. Stress marker index indices and antioxidants may be measured in brain (invasively and non-invasively), CSF, plasma, serum, erythrocytes, urine, and saliva, (e.g. alpha amylase). Corticotropin-releasing factor (CRF) and the related urocortin peptides are other examples of stress markers.

The time window or space-state over which the various indices are quantified can have any desired duration, and if a second time window or space-state is used, it can have any desired second duration. The first time window or space-state and the second time window or space-state can have any relationship. The two time windows may be overlapping, partially overlapping, contiguous, or non-contiguous, and the second time window or space-state may be a subwindow of the first time window or space-state. In other words, the second time window or space-state may be fully overlapped by the first time window or space-state.

In another embodiment, the first time window or space-state and the second time window or space-state are non-contiguous. In other words, the first and second time window or space-states do not overlap and there exists a temporal gap between them.

Embodiments of the present invention also comprise comparing the at least one index to at least one reference value associated with the at least one index. In addition, if at least one second index has been determined as described above, the method can comprise comparing the at least one second index or marker to at least one second reference value associated with the at least one second index.

The reference values can be preselected, selected from a finite set of predetermined options, or can be dynamically recalculated during performance of the method. They may be determined from the patient's history or from a set of normative data. For example, the reference values can be prior values of the index. For example, if the index value is heart rate variability (HRV), the corresponding reference value can be a single value defined by a physician in view of the patient's age, sex, fitness level, body mass index, physical fitness level at the time of the measurement, initial disease state, or other values; it can be a value chosen from a set of predetermined options relating to different typical initial disease states or the like; or it can be dynamically recalculated, such as from an indicator of central tendency (e.g., a mean, a median, or a percentile value) of HRV data over one or more timescales, such as the past hour, day, week, month, or year, among others, to account for ultradian, circadian, catamenial, lunar, and seasonal variations.

In one embodiment, comparing the at least one first index to the at least one first reference value, the at least one second index to the at least one second reference value, or both comprises determining a statistical relationship (which may be linear or non-linear, positive or negative) between the index or indices and the reference value or values. For example, the statistical relationship may be a number of standard deviations, percentile ranks, or the like between the reference value and the corresponding index.

The comparison may involve, when applicable, using spectral analysis, high order spectral analysis, detrended fluctuation analysis, fractal analysis, multifractal analysis, correlation dimension, and combinations thereof. For example, the comparison may involve determining the slope of a trendline of data points, the shape of a curve of data points, the smoothness of a set of data points, or an autocorrelation of a set of data points, among others.

The terms "index" refers to values, quantities, classes, categories or items derived from signals (raw or processed). The term "reference" corresponds to quantities, classes, categories or items derived from signals (raw or processed) recorded from a subject in the past (recent or distant) or obtained from tables of comparable normative values obtained from other normal or diseased subjects. For example, the HRV calculated from data collected over a period time ending in the present day (the index) may be compared to HRV calculated from data collected over an identical period of time 1 year earlier (the reference). The index as specified above may be also compared to HRV calculated from subjects that match the demographic and clinical characteristics (the other reference) of the subject in question. Determination about the state of the subject's disease may be made by using either or both of the references. For example, a cognitive (e.g. verbal memory) or EEG index (e.g., power in the alpha band) calculated from data collected from a subjects over a period time ending in the present day (the index), may be compared to verbal memory or alpha band power calculated from data collected from over an identical period of time 1 year earlier (the reference) and to a third period of time, three years earlier. These indices as specified above may be also compared to verbal memory and alpha band power obtained from subjects that match the demographic and clinical characteristics (the other reference) of the subject in question. Determination about the state of the subject's disease may be made by using either or both of the references.

In one embodiment, comparing the at least one index to the at least one reference value comprises determining a non-linear relationship between the index or indices and the reference value or values. For example, the non-linear relationship may be related to a pattern matching relationship or a non-linear mathematic relationship between the reference value and the corresponding index.

Also, embodiments of the present invention comprises assessing a state of a disease or a body system of the patient based on comparing the at least one index to the at least one reference value. If at least one second index is received, assessing can be further based on comparing the at least one second index to the at least one second reference value. For example, a second index and a third index can be received, and assessing can further based on comparing the second index to a second reference value and comparing the third index to a third reference value.

In a further embodiment, embodiments of the present invention further comprise receiving at least one third autonomic index, neurologic index, stress marker index, psychiatric index, an endocrine index, an adverse effect of therapy index, a physical fitness index, or quality of life index of a patient over a third time window. In this further embodiment, the method also further comprises comparing the at least one third index to at least one third reference value. In this further embodiment, assessing the state of the disease of the patient is based on comparing the at least one first index to the at least one first reference value associated with the at least one first index, the at least one second index to the at least one second reference value associated with the at least one second index, and the at least one third index to the at least one third reference value associated with the at least one third index.

Figure 3A:
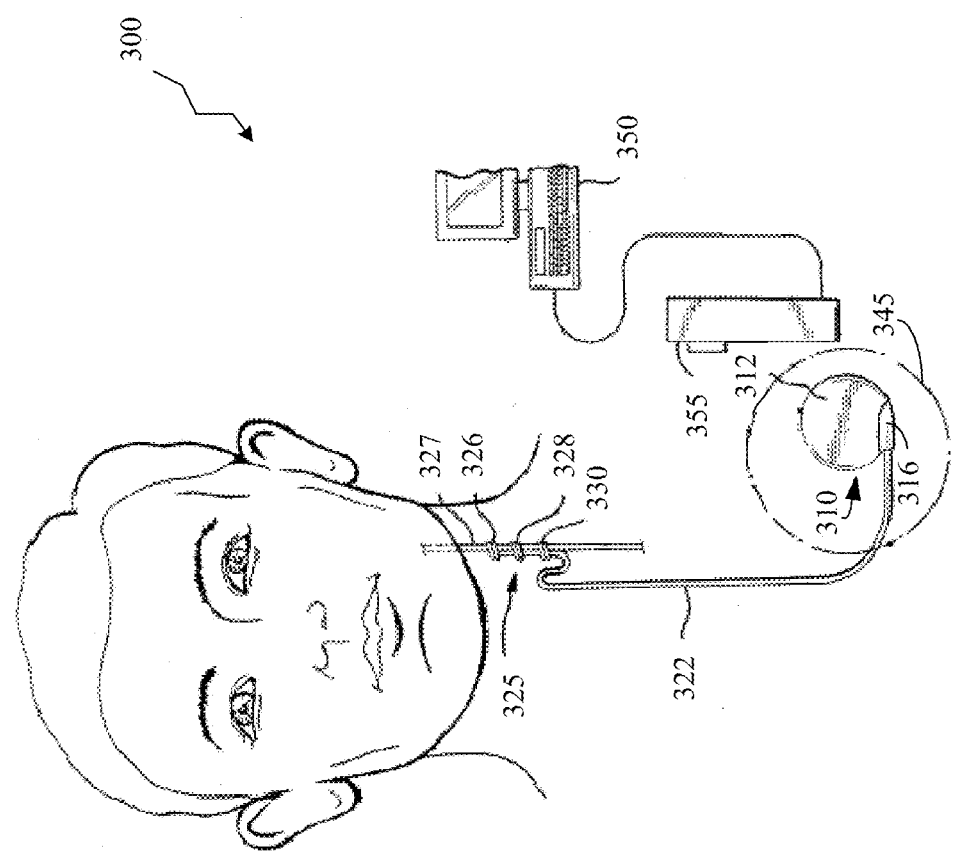
FIG. 3A provides a stylized diagram of a medical device implanted into a patient's body, in accordance with one illustrative embodiment of the present invention.

Although not limited to the following, exemplary systems capable of implementing embodiments of the present invention are described below. FIG. 3A depicts a stylized implantable medical system (IMD) 300 for implementing one or more embodiments of the present invention. An electrical signal generator 310 is provided, having a main body 312 comprising a case or shell with a header 316 for connecting to an insulated, electrically conductive lead assembly 322. The generator 310 is implanted in the patient's chest in a pocket or cavity formed by the implanting surgeon just below the skin (indicated by a dotted line 345), similar to the implantation procedure for a pacemaker pulse generator.

A nerve electrode assembly 325, preferably comprising a plurality of electrodes having at least an electrode pair, is conductively connected to the distal end of the lead assembly 322, which preferably comprises a plurality of lead wires (one wire for each electrode). Each electrode in the electrode assembly 325 may operate independently or alternatively, may operate in conjunction with the other electrodes. In one embodiment, the electrode assembly 325 comprises at least a cathode and an anode. In another embodiment, the electrode assembly comprises one or more unipolar electrodes.

Lead assembly 322 is attached at its proximal end to connectors on the header 316 of generator 310. The electrode assembly 325 may be surgically coupled to the vagus nerve 327 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 325 comprises a bipolar stimulating electrode pair 326, 328 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 325 may be secured to the vagus nerve 327 by a spiral anchoring tether 330 such as that disclosed in U.S. Pat. No. 4,979,511 issued Dec. 25, 1990 to Reese S. Terry, Jr. Lead assembly 322 may be secured, while retaining the ability to flex with movement of the chest and neck, by a suture connection to nearby tissue (not shown).

In alternative embodiments, the electrode assembly 325 may comprise temperature sensing elements, blood pressure sensing elements, and/or heart rate sensor elements. Other sensors for other body parameters may also be employed. Both passive and active stimulation may be combined or delivered by a single IMD according to the present invention. Either or both modes may be appropriate to treat a specific patient under observation.

Figure 3B:
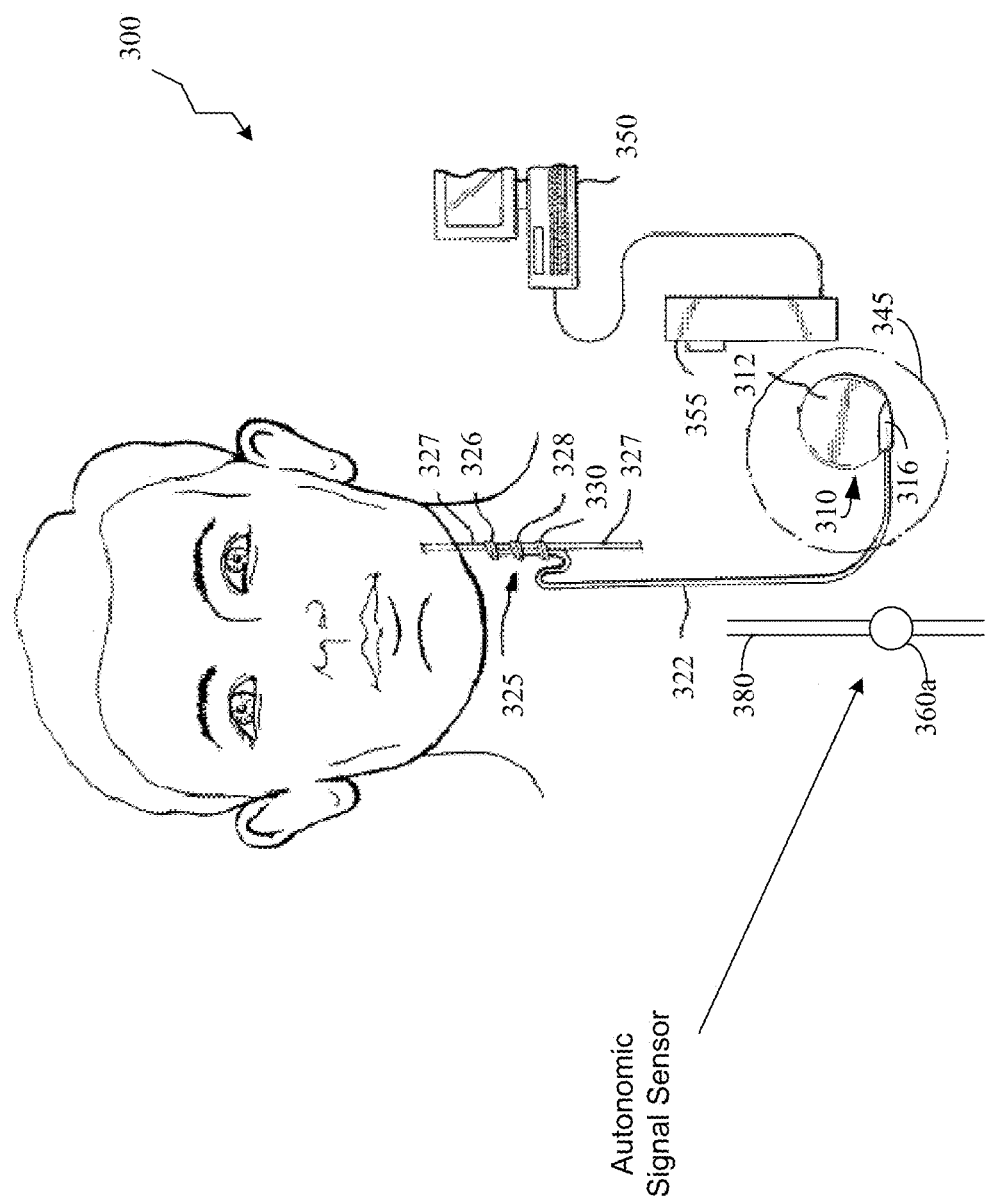
FIG. 3B provides a stylized diagram of a medical device implanted into a patient's body, in accordance with one illustrative embodiment of the present invention.

In alternative embodiments, the implantable medical device system further comprises an electrical stimulator comprising an autonomic signal sensor 360a (not to scale) adapted to be coupled to a body part, such as an internal organ 380 (FIG. 3B) or a neurologic signal sensor 360n (also not to scale) adapted to record (either non-invasively or invasively) from a portion of the nervous system, such as the frontal cortex 390 (FIG. 3C) or another region of the brain. The physician can select precise locations for coupling to the internal organ 380 or frontal cortex 390 (or other portion of the nervous system) based on his or her observations of the patient's medical condition, among other values. In various embodiments, the implantable medical device system may comprise one, two, or three of the IMD 300, the autonomic signal sensor 360a, and the neurologic signal sensor 360n.

The electrical pulse generator 310 may be programmed with an external device (ED) such as computer 350 using programming software known in the art. A programming wand 355 may be coupled to the computer 350 as part of the ED to facilitate radio frequency (RF) communication between the computer 350 and the pulse generator 310. The programming wand 355 and computer 350 permit non-invasive communication with the generator 310 after the latter is implanted. In systems where the computer 350 uses one or more channels in the Medical Implant Communications Service (MICS) bandwidths, the programming wand 355 may be omitted to permit more convenient communication directly between the computer 350 and the pulse generator 310.

Figure 4:
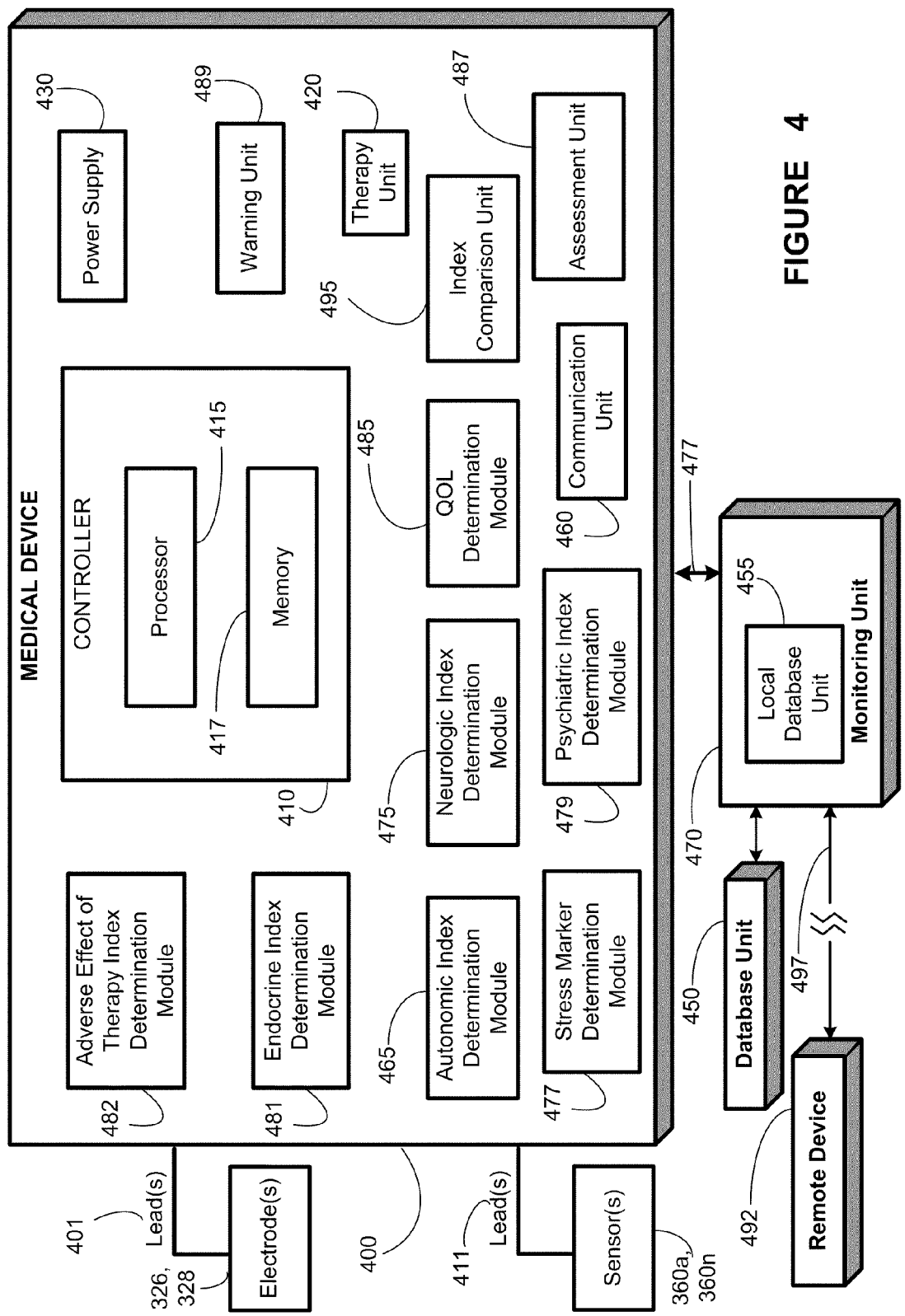
FIG. 4 is a block diagram of an implantable medical device system, in accordance with one illustrative embodiment of the present invention.

Turning now to FIG. 4, a block diagram depiction of a medical device 400 is provided, in accordance with one illustrative embodiment of the present invention.

In some embodiments, the medical device 400 may be implantable (such as implantable electrical signal generator 310 from FIG. 3), while in other embodiments the medical device 400 may be completely external to the body of the patient.

The medical device 400 (such as generator 310 from FIG. 3) may comprise a controller 410 capable of controlling various aspects of the operation of the medical device 400. The controller 410 is capable of receiving internal data or external data, and in one embodiment, is capable of causing a therapy unit 420 (FIG. 4) to generate and deliver an electrical signal to target tissues of the patient's body for treating a medical condition. For example, the controller 410 may receive manual instructions from an operator externally, or may cause the electrical signal to be generated and delivered based on internal calculations and programming. The controller 410 is capable of affecting substantially all functions of the medical device 400.

The controller 410 may comprise various components, such as a processor 415, a memory 417, etc. The processor 415 may comprise one or more microcontrollers, microprocessors, etc., capable of performing various executions of software components. The memory 417 may comprise various memory portions where a number of types of data (e.g., internal data, external data instructions, software codes, status data, diagnostic data, etc.) may be stored. The memory 417 may comprise one or more of random access memory (RAM), dynamic random access memory (DRAM), electrically erasable programmable read-only memory (EEPROM), flash memory, etc.

As stated above, in one embodiment, the medical device 400 may also comprise a therapy unit 420 capable of generating and delivering electrical signals to one or more electrodes 326, 328 via leads 401 (FIG. 4). A lead assembly such as lead assembly 322 (FIG. 3) may be coupled to the medical device 400. Therapy may be delivered to the leads 401 comprising the lead assembly 322 by the therapy unit 420 based upon instructions from the controller 410. The therapy unit 420 may comprise various circuitry, such as electrical signal generators, impedance control circuitry to control the impedance "seen" by the leads, and other circuitry that receives instructions relating to the delivery of the electrical signal to tissue. The therapy unit 420 is capable of delivering electrical signals over the leads 401 comprising the lead assembly 322. As should be apparent, in certain embodiments, the medical device 400 does not comprise a therapy unit 420, lead assembly 322, or leads 401.

In other embodiments, a lead 401 is operatively coupled to an electrode, wherein the electrode is adapted to couple to at least one of a portion of a brain structure of the patient, a cranial nerve of a patient, a spinal cord of a patient, a sympathetic nerve structure of the patient, or a peripheral nerve of the patient.

The medical device 400 may also comprise a power supply 430. The power supply 430 may comprise a battery, voltage regulators, capacitors, etc., to provide power for the operation of the medical device 400, including delivering the therapeutic electrical signal. The power supply 430 comprises a power source that in some embodiments may be rechargeable. In other embodiments, a non-rechargeable power source may be used. The power supply 430 provides power for the operation of the medical device 400, including electronic operations and the electrical signal generation and delivery functions. The power supply 430 may comprise a lithium/thionyl chloride cell or a lithium/carbon monofluoride (LiCFx) cell if the medical device 400 is implantable, or may comprise conventional watch or 2V batteries for external (i.e., non-implantable) embodiments. Other battery types known in the art of medical devices may also be used.

The medical device 400 may also comprise a communication unit 460 capable of facilitating communications between the medical device 400 and various devices. In particular, the communication unit 460 is capable of providing transmission and reception of electronic signals to and from an monitoring unit 470, such as a handheld computer or PDA that can communicate with the medical device 400 wirelessly or by cable. The communication unit 460 may include hardware, software, firmware, or any combination thereof.

The medical device 400 may also comprise one or more sensor(s) 360a, 360n coupled via sensor lead(s) 411 to the medical device 400. Sensor(s) 360a are capable of receiving signals related to an autonomic index, such as the patient's heart beat, blood pressure, and/or temperature, among others, and delivering the signals to the medical device 400. Sensor(s) 360n are capable of receiving signals related to a neurologic index, and delivering the signals to the medical device 400. In one embodiment, the sensor(s) 360a, 360n may be the same as implanted electrode(s) 326, 328 (FIG. 3). In other embodiments, the sensor(s) 360a, 360n are separate structures that may be placed on the patient's skin, such as over the patient's heart or elsewhere on the patient's body. The sensor(s) 360a, 360n and accompanying leads may be considered an interface for the medical device 400 to receive, e.g., at least one of autonomic data, neurologic data, or stress data, such as from the sensors 360a, 360n.

Exemplary sensor(s) 360a include electrocardiography (EKG) devices, accelerometers, inclinometers, pupillometers, face or body temperature monitors, skin resistance monitors, and/or sound and pressure sensors, among others known to the person of ordinary skill in the art having the benefit of the present disclosure.

Alternatively or in addition to sensors 360, the medical device 400 can comprise at least one interface (not shown) capable of receiving data relating to at least one index. For example, the interface can receive data comprising index values. Alternatively or in addition, the interface can receive data further processible by other components of the medical device 400.

The medical device may also comprise at least one of an autonomic index determination unit 465 capable of determining at least one autonomic index, a neurologic index determination unit 475 capable of determining at least one neurologic index, a stress marker index determination unit 477 capable of determining at least one stress marker index, a psychiatric index determination unit 479 capable of determining at least one psychiatric index, an endocrine index determination unit 481 capable of determining at least one endocrine index, an adverse effect of therapy index determination unit 482 capable of determining at least one adverse effect of therapy index, or a quality of life (QOL) index determination unit 485 capable of determining at least one quality of life index. If present, the autonomic index determination unit 465 can receive signals related to an autonomic index delivered to the medical device 400 and, from them, determine an autonomic index. The autonomic index determination unit 465 will be discussed in more detail below. Similarly, if present, the neurologic index determination unit 475 can receive signals related to a neurologic index delivered to the medical device 400 and, from them, determine a neurologic index. The neurologic index determination unit 475 will be discussed in more detail below. Similarly, if present, the QOL index determination unit 485 can receive signals related to a QOL index delivered to the medical device 400, such as through the communication unit 460 and, from them, determine a QOL index. In one embodiment, the signals related to a QOL index are sent from a remote device 492 that is capable of gathering such signals. In another embodiment, the QOL index determination unit 485 is located in remote device 492.

Also, similarly, if present, the stress marker index determination unit 477 can receive signals related to a stress marker index delivered to the medical device 400 and, from them, determine a stress marker index. Also, if present, the psychiatric index determination unit 479 can receive signals related to an psychiatric index delivered to the medical device 400 and, from them, determine an psychiatric index. Similarly, if present, the endocrine index determination unit 481 can determine at least one endocrine index and/or the adverse effect of therapy index determination unit 482 can determine at least one adverse effect of therapy index. The stress marker index determination unit 477, psychiatric index determination unit 479, endocrine index determination unit 481, and one adverse effect of therapy index determination unit 482 are discussed in more detail elsewhere herein.

The medical device 400 can also comprise an index comparison unit 495 capable of comparing at least one index with at least one reference value. The reference value may be stored in the memory 417, in a local database unit 455, a database unit 450, or a remote device 492. The index comparison unit 495 will be discussed in more detail below.

The medical device 400 can also comprise a assessment unit 487 capable of assessing a state of a disease of a patient based on at least one output of the index comparison unit.

The medical device 400 can also comprise a warning unit 489 capable of providing a warning signal to the patient, a physician, or a caregiver if assessing indicates disease progression. In one embodiment, the warning signal is proportional to at least one of a magnitude of a change of a progression, a rate of change of a disease progression, or a correlation of the index value to life span.

The medical device 400 can also comprise a therapy unit adapted to deliver a therapy for the disease to a patient. For example, the medical device 400 can comprise a therapy unit 420 and related hardware, such as lead(s) 401 and electrode(s) 326, 328.

Although not shown, the medical device 400 can comprise an acute disease state detection unit adapted to detect an acute disease state in the patient. For example, the acute disease state detection unit can be adapted to detect an epileptic event. Common epileptic events of concern are, for example, clinical seizures, subclinical seizures, loss of consciousness, falls to the ground, cognitive impairment during and following a seizure, prolonged confusional states, bodily injuries, alterations in heart, respiratory and in other functions under autonomic control, sudden unexpected death, psychosis, depression, suicide, osteoporosis, obesity, and reproductive dysfunction. Exemplary acute disease state detection units are known to the person of ordinary skill in the art and can be included in the medical device 400 as a matter of routine experimentation for those of ordinary skill in the art having the benefit of the present disclosure.

Figure 5:
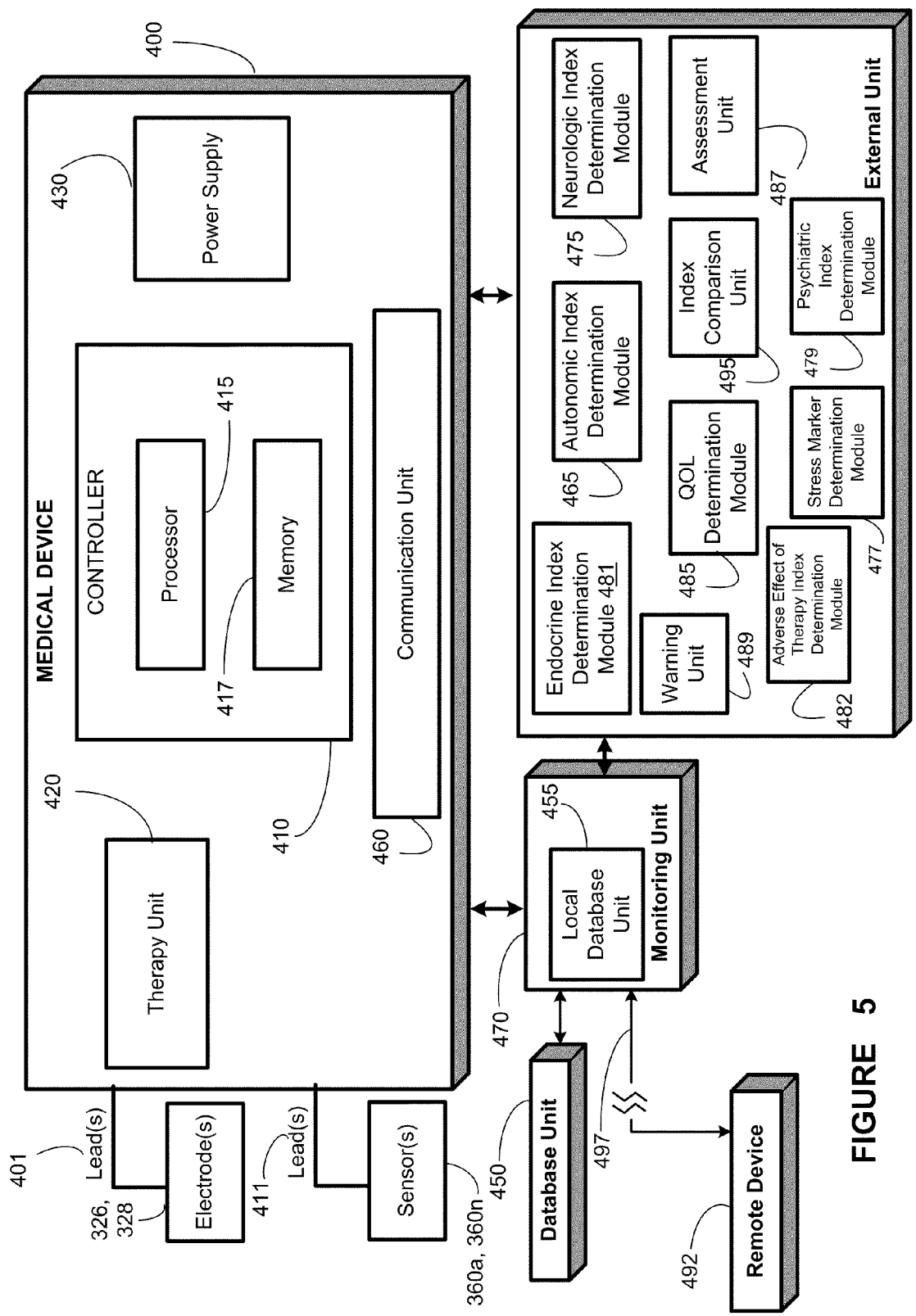
FIG. 5 is a block diagram of a medical device system that includes a medical device and an external unit, in accordance with one illustrative embodiment of the present invention.

FIG. 5 shows a medical device system similar to that shown in FIG. 4, but with several elements located in an external device not implanted in the patient. Specifically, FIG. 5 depicts a medical device system with the following elements located in an external disease state unit: the autonomic index determination unit 465, the neurologic index determination unit 475, the stress marker index determination unit 477, the psychiatric index determination unit 479, the endocrine index determination unit 481, the adverse effect of therapy index determination unit 482, the QOL index determination unit 485, the index comparison unit 495, and the assessment unit 487 are located in an external disease state unit. Housing these elements in an external disease state unit may permit use of more complex analysis tools and algorithms because an externally unit generally can have a faster microprocessor (which consume more power and generate more heat), more memory, and AC power or larger batteries than an implanted device. For example, this embodiment of FIG. 5 may be useful if the calculations performable by the determination modules 465, 475, 477, 479, 485 or the units 495, 487 are so complex and/or dependent on such a large number of data lookups (e.g., in a local database unit 455 or a database unit 450) that performing the calculations in the medical device 400 would consume too much power or generate too much heat.

Figure 6:
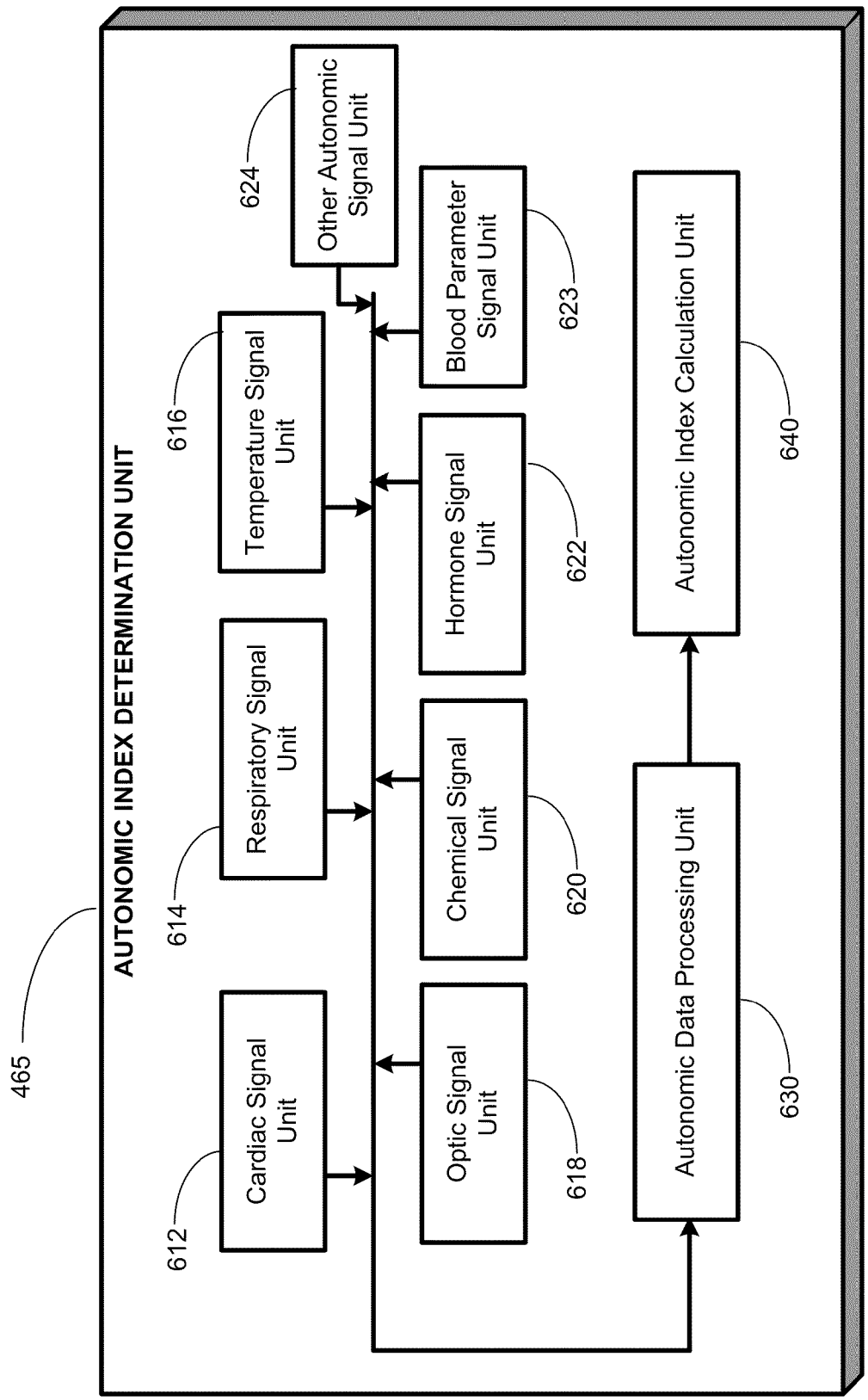
FIG. 6 is a stylized block diagram of an autonomic index unit of a medical device or medical device system, in accordance with one illustrative embodiment of the present invention.

Turning to FIG. 6, an autonomic index determination unit 465 is shown in more detail. The autonomic index determination unit 465 can comprise a cardiovascular signal unit 612 capable of processing at least one cardiovascular indication received from sensor(s) 360a. Alternatively or in addition, the autonomic index determination unit 465 can comprise a respiratory signal unit 614 capable of processing at least one respiratory indication received from sensor(s) 360a. Alternatively or in addition, the autonomic index determination unit 465 can comprise a blood parameter signal unit 623 capable of processing at least one blood parameter indication (e.g., blood glucose, blood pH, etc). Alternatively or in addition, the autonomic index determination unit 465 can comprise a temperature signal unit 616 capable of processing at least one temperature indication received from sensor(s) 360a. Alternatively or in addition, the autonomic index determination unit 465 can comprise an optic signal unit 618 capable of processing at least one optic indication received from sensor(s) 360a. Alternatively or in addition, the autonomic index determination unit 465 can comprise a chemical signal unit 620 capable of processing at least one body chemical indication received from sensor(s) 360a. Alternatively or in addition, the autonomic index determination unit 465 can comprise a hormone signal unit 622 capable of processing at least one hormone indication received from sensor(s) 360a. Alternatively or in addition, the autonomic index determination unit 465 can comprise one or more other autonomic signal unit(s) 624, such as a skin resistance signal unit.

The autonomic index determination unit 465 can also comprise an autonomic data processing unit 630. The autonomic data processing unit 630 can perform any filtering, noise reduction, amplification, or other appropriate processing of the data received by the signal units 612-624 desired by the person of ordinary skill in the art prior to calculation of the autonomic index.

The autonomic index determination unit 465 can also comprise an autonomic index calculation unit 640. The autonomic index calculation unit 640 can calculate an autonomic index from the data passed by the autonomic data processing unit 630.

For example, the autonomic index calculation unit 640 may calculate the heart rate, a change in the heart rate, the speed of change in heart rate, blood pressure, heart sounds, heart rhythm, heartbeat wave morphology, heartbeat complex morphology, or the shape of the deflection of the thoracic wall as the heart apex beats against it, among others, from cardiovascular data received by cardiovascular signal unit 612.

For another example, the autonomic index calculation unit 640 may calculate the respiration (breath) rate, respiration pattern, airflow velocity, respiration amplitude (tidal volume), oxygen saturation, arterial gas concentrations, or blood pH, among others, from respiratory data received by respiratory signal unit 614.

For still another example, the autonomic index calculation unit 640 may calculate a change in the skin temperature or skin resistance of a part of the patient's face or a change in the core temperature of the patient, from temperature data received by temperature signal unit 616.

Figure 7:
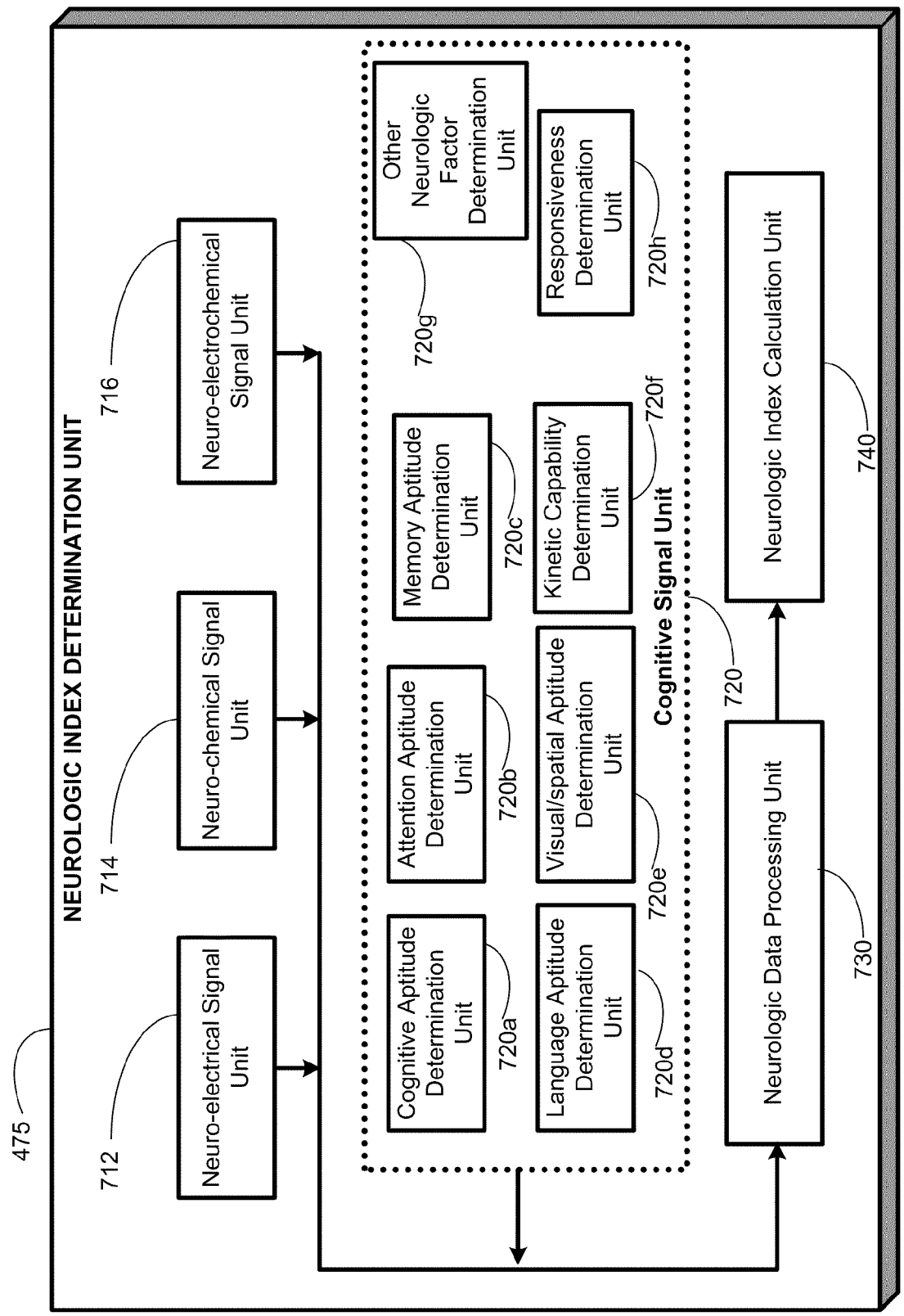
FIG. 7 is a stylized block diagram of a neurologic index unit of a medical device or medical device system, in accordance with one illustrative embodiment of the present invention.

Turning to FIG. 7, an exemplary embodiment of a neurologic index determination unit 475 is shown. The neurologic index determination unit 475 can comprise at least one of a neuro-electrical signal unit 712 capable of processing at least one neuro-electrical signal received from a sensor 360*n*; a neuro-chemical signal unit 714 capable of processing at least one neuro-chemical signal received from a sensor 360*n*; a neuro-electrochemical signal unit 716 capable of processing at least one neuro-electrochemical signal received from a sensor 360*n*; or a cognitive signal unit 720 capable of processing at least one cognitive indication received from a sensor 360*n* or another device, such as a remote device 492.

In one embodiment, the cognitive signal unit comprises at least one of a cognitive aptitude determination unit 720*a* capable of processing at least one cognitive aptitude indication; an attention aptitude determination unit 720*b* capable of processing at least one attention aptitude indication; a memory aptitude determination unit 720*c* capable of processing at least one memory indication; a language aptitude determination unit 720*d* capable of processing at least one language indication; a visual/spatial aptitude determination unit 720*e* capable of processing at least one visual/spatial indication; a kinetic capability determination unit 720*f* capable of processing at least one kinetic indication; one or more other neurologic factor determination unit(s) 720*g*; or a responsiveness determination unit 720*h*.

The neurologic index determination unit 475 can also comprise a neurologic data processing unit 730. The neurologic data processing unit 730 can perform any filtering, noise reduction, amplification, or other appropriate processing of the data received by the signal units 712-720*g* desired by the person of ordinary skill in the art prior to calculation of the neurologic index.

The neurologic index determination unit 475 can also comprise a neurologic index calculation unit 740. The neurologic index calculation unit 740 can calculate a neurologic index from the data passed by the neurologic data processing unit 730.

For example, the neurologic index calculation unit 740 may calculate a brain index, such as those determinable from signals yielded by an EEG, ECoG, or depth electrode (i.e., a deep brain electrode) as sensor(s) 360*n*, as received by neuro-electrical signal unit 712, neuro-chemical signal unit 714, and/or neuro-electrochemical signal unit 716 and, optionally, further processed by neurologic data processing unit 730.

The brain index can also be calculated using other neurological signals. For example, sensor(s) 360*n* can detect spikes in neurons or axons in the brain and spinal cord including central structures and pathways with autonomic control or modulatory capabilities, cranial nerves (e.g., vagus nerve), autonomic ganglia or nerves and peripheral nerves. Sensor(s) 360*n* can also detect neural imaging or brain imaging signals including, for example: Functional Magnetic Resonance Imaging (fMRI), Magnetoencephalography (MEG), Positron Emission Tomography (PET), Event-Related Optical Signal (EROS), and Diffuse Optical Imaging (DOI)). Other imaging techniques such as voltage-senstive dyes, ultrasound, infrared, near infra-red and other forms of thermography. Qualitative or descriptive and quantitative (e.g. volumetrics) data obtained from devices that are not part of this system (e.g., MRI equipment) may be uploaded and stored into this system for assessing disease state.

For another example, the neurologic index calculation unit 740 may calculate a body kinetic index, such as the body's (or of a portion thereof such as an arm or a leg) acceleration, direction, position, smoothness, amplitude, or force of movements, and whether there are extraneous or abnormal body oscillations during resting conditions or movement. The body kinetic index may be determinable by electromyography, a mechanogram, an accelerometer, and/or an inclinometer as sensor(s) 360*n*, as received by kinetic capability determination unit 720*f*, and, optionally, further processed by neurologic data processing unit 730.

Kinetic indices are voluntary or involuntary motor acts that provide insight into the functional state of the nervous system and are thus classified as a neurologic index. The ability to perform movements: a) in any direction; b) do it smoothly and with precision so that for example, a target (e.g. putting a key into its hole) may be met in the first attempt or handwriting is legible; c) changing direction to avoid colliding with an object interposed on its path to a target and re-adjusting the trajectory to reach the original target; and d) with adaptive force and discriminations so to be able to pick a penny off a flat surface and also lift heavy objects. The acceleration and velocity speed, direction and smoothness may be quantified using tools such as 3-D accelerometers among others.

Even though physical fitness indices depend to some extent on the integrity of kinetic indices, in this invention they are considered as distinct from kinetic indices. Physical fitness indices are used to assess physical fitness through certain measures as described herein. A person who leads a sedentary life is physically unfit but may have normal kinetic indices.

Figure 8:
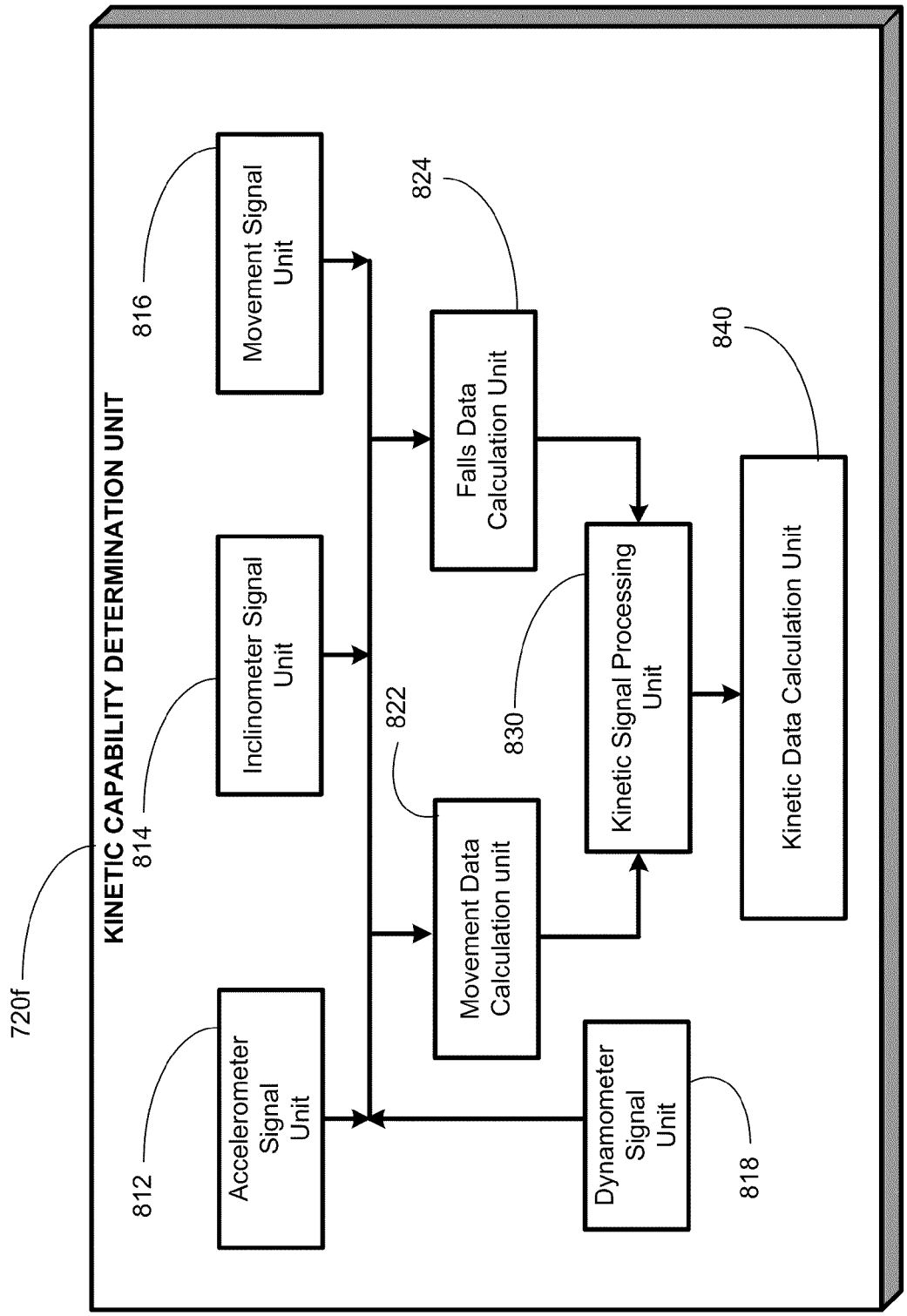
FIG. 8 is a stylized block diagram of a kinetic capability determination unit of a medical device or medical device system, in accordance with one illustrative embodiment of the present invention.

FIG. 8 shows a kinetic capability determination unit 720*f* in more detail. The kinetic capability determination unit 720*f* can be capable of receiving at least one of an accelerometer signal, an inclinometer signal, a movement signal, or a dynamometer (force) signal via accelerometer signal unit 812, inclinometer signal unit 814, movement signal unit 816, or dynamometer signal unit 818, respectively. From the at least one of the accelerometer signal, the inclinometer signal, the movement signal, or a dynamometer signal, one or more of movement data or falls data can be calculated by movement data calculation unit 822 or falls data calculation unit 824, respectively. The calculated movement data and/or falls data can be processed by kinetic signal processing unit 830, and thereafter, kinetic data calculated by kinetic data calculation unit 840.

Figure 9:
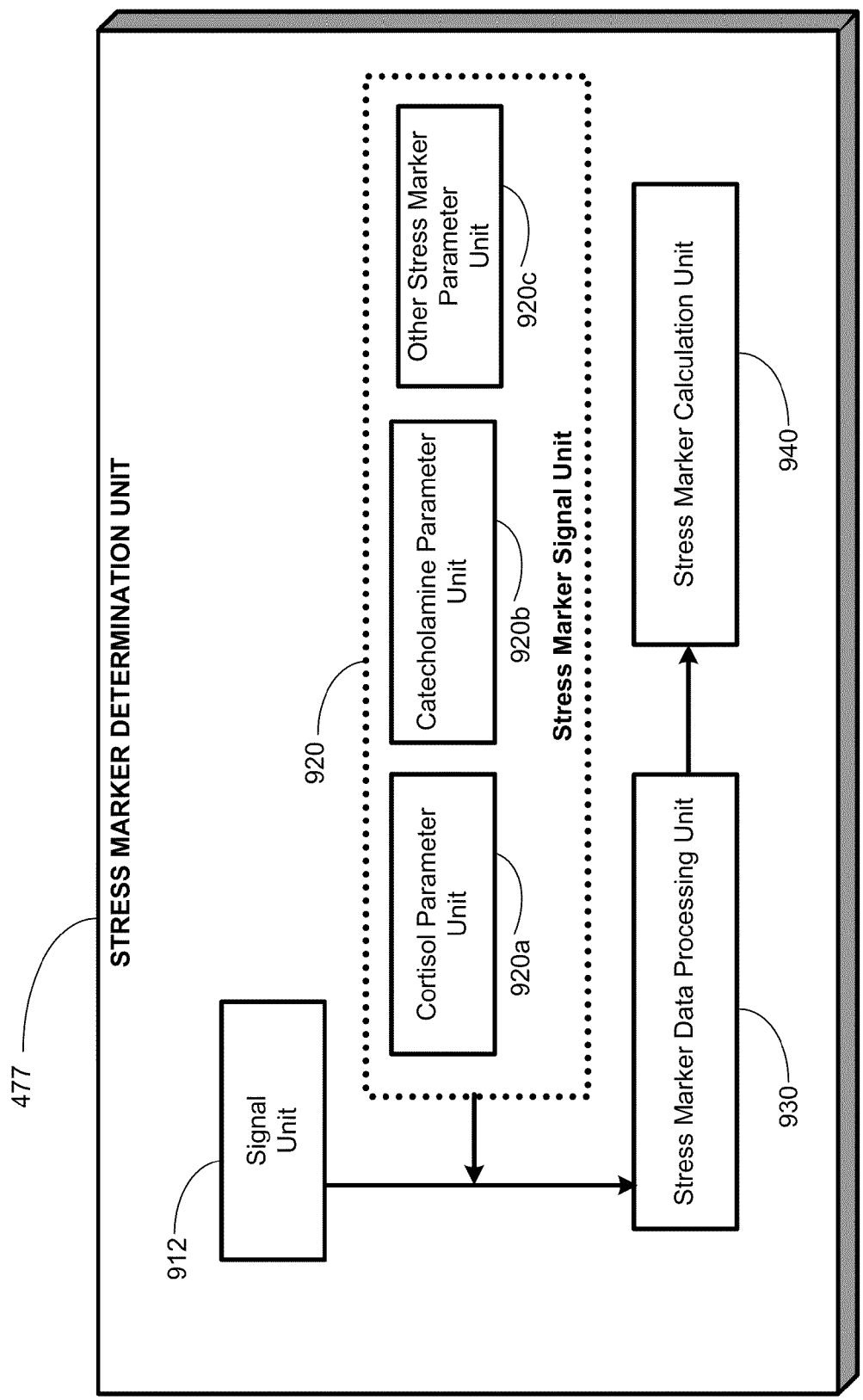
FIG. 9 is a stylized block diagram of a stress marker index unit of a medical device or medical device system, in accordance with one illustrative embodiment of the present invention.

Turning to FIG. 9, an exemplary embodiment of a stress marker index determination unit 477 is shown. The stress marker index determination unit 477 can comprise at least one signal unit 912, capable of receiving a signal as described above from which a stress marker index can be derived, such as a cortisol parameter unit 920*a*, a catecholamine parameter signal unit 920*b*, and/or another stress marker parameter unit 920*c*.

The stress marker index determination unit 477 can also comprise a stress marker index data processing unit 930. The stress marker index data processing unit 930 can perform any filtering, noise reduction, amplification, or other appropriate processing of the data received by the signal unit 912 desired by the person of ordinary skill in the art prior to calculation of the stress marker index.

The stress marker index determination unit 477 can also comprise a stress marker index calculation unit 940. The stress marker index calculation unit 940 can calculate a stress marker index from the data passed by the stress marker index processing unit 930. For example, the stress marker index calculation unit 940 may calculate a stress marker index as received by signal unit 912 and, optionally, further processed by stress marker index data processing unit 930.

Figure 10:
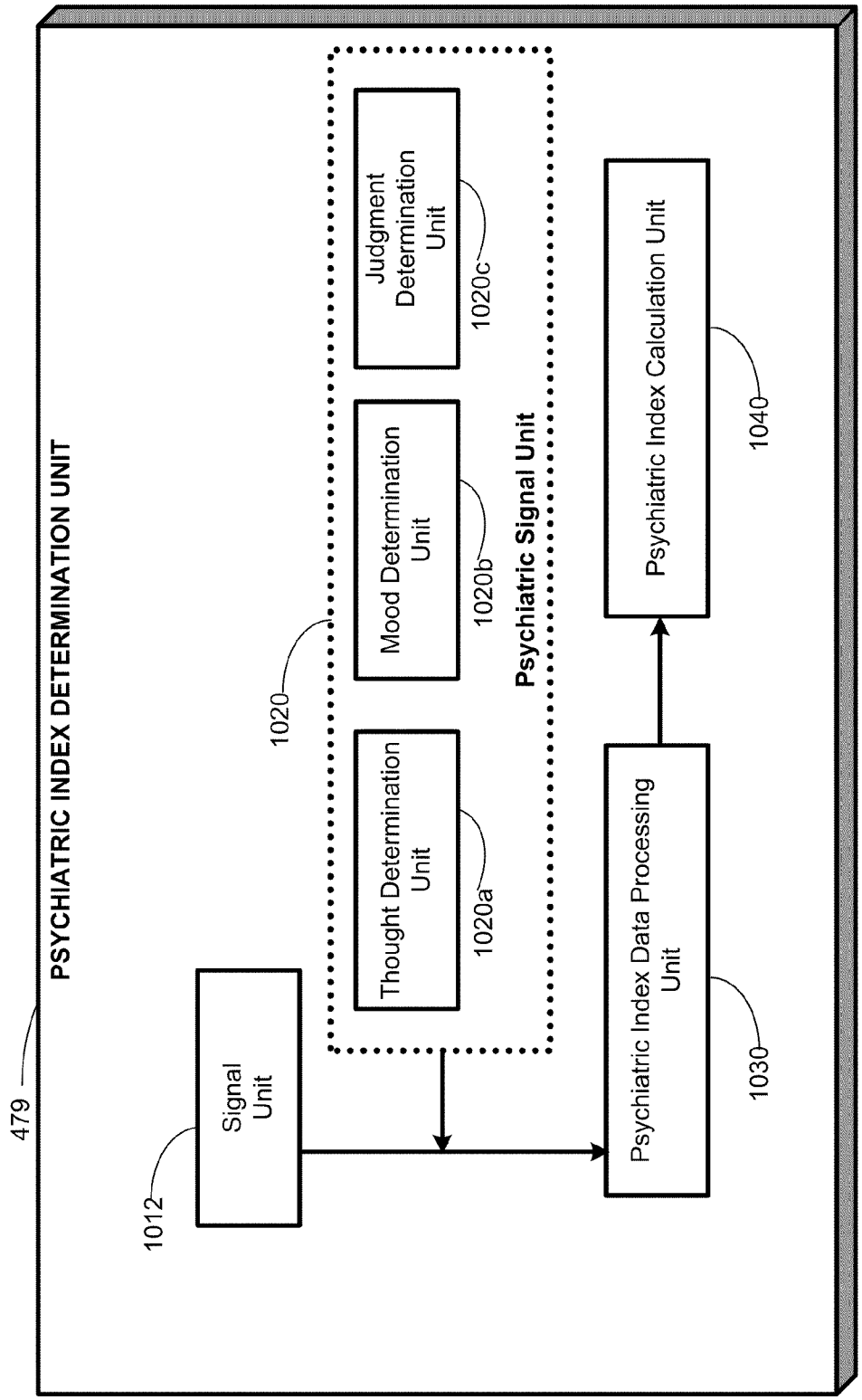
FIG. 10 is a stylized block diagram of a psychiatric index unit of a medical device or medical device system, in accordance with one illustrative embodiment of the present invention.

Turning to FIG. 10, an exemplary embodiment of a psychiatric index determination unit 479 is shown. The psychiatric index determination unit 479 can comprise at least one signal unit 1012, capable of receiving a signal as described above from which a psychiatric index can be derived. For example, the psychiatric index determination unit 479 can comprise a psychiatric signal unit 1020, comprising one or more of a thought determination unit 1020a, a mood determination unit 1020b, or a judgment determination unit 1020c. The various determination units 1020a-c can use tests or scales discussed above to make a determination, e.g., by administering a test known to the person of ordinary skill in the art to provide information regarding the subject's thought, mood, or judgment, or receiving the results of such a test from an external source.

The psychiatric index determination unit 479 can also comprise a psychiatric index data processing unit 1030. The psychiatric index data processing unit 1030 can perform any filtering, noise reduction, amplification, or other appropriate processing of the data received by the signal unit 1012 desired by the person of ordinary skill in the art prior to calculation of the psychiatric index.

The psychiatric index determination unit 479 can also comprise a psychiatric index calculation unit 1040. The psychiatric index calculation unit 1040 can calculate a psychiatric index from the data passed by the psychiatric index processing unit 1030.

For example, the psychiatric index calculation unit 1040 may calculate a psychiatric index as received by signal unit 1012 and, optionally, further processed by psychiatric index data processing unit 1030.

Figure 11:
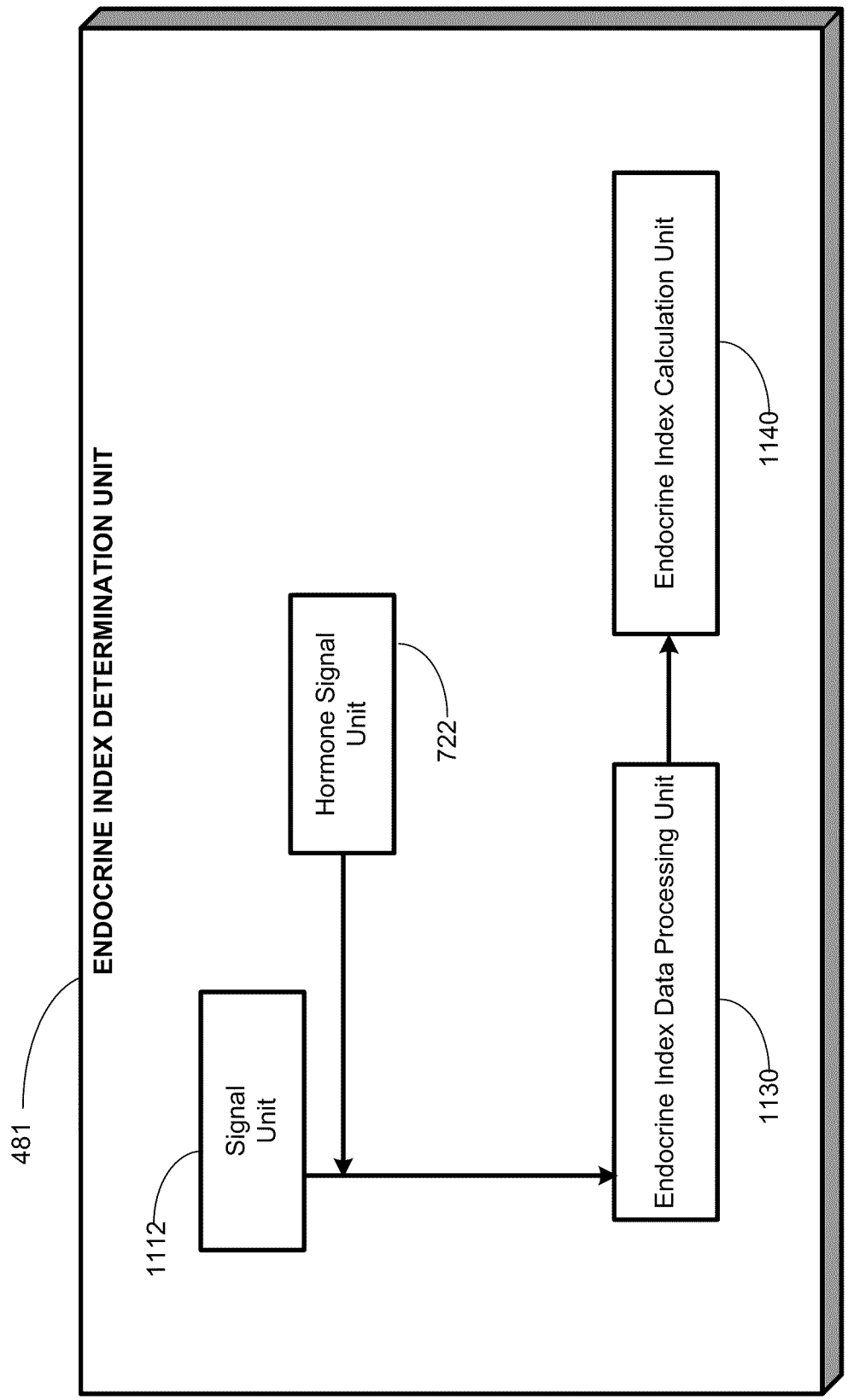
FIG. 11 is a stylized block diagram of an endocrine index unit of a medical device or medical device system, in accordance with one illustrative embodiment of the present invention.

Turning to FIG. 11, an exemplary embodiment of an endocrine index determination unit 481 is shown. The endocrine index determination unit 481 can comprise at least one signal unit 1112, capable of receiving a signal as described above from which an endocrine index can be derived. In a particular embodiment, as depicted, the endocrine index determination unit 481 can comprise a hormone signal unit 722, as described above.

The endocrine index determination unit 481 can also comprise an endocrine index data processing unit 1130. The endocrine index data processing unit 1130 can perform any filtering, noise reduction, amplification, or other appropriate processing of the data received by the signal unit(s) 1112, 722 desired by the person of ordinary skill in the art prior to calculation of the endocrine index.

The endocrine index determination unit 481 can also comprise an endocrine index calculation unit 1140. The endocrine index calculation unit 1140 can calculate an endocrine index from the data passed by the endocrine index processing unit 1130.

For example, the endocrine index calculation unit 1140 may calculate an endocrine index as received by signal unit(s) 1112, 722 and, optionally, further processed by endocrine index data processing unit 1130.

Figure 12:
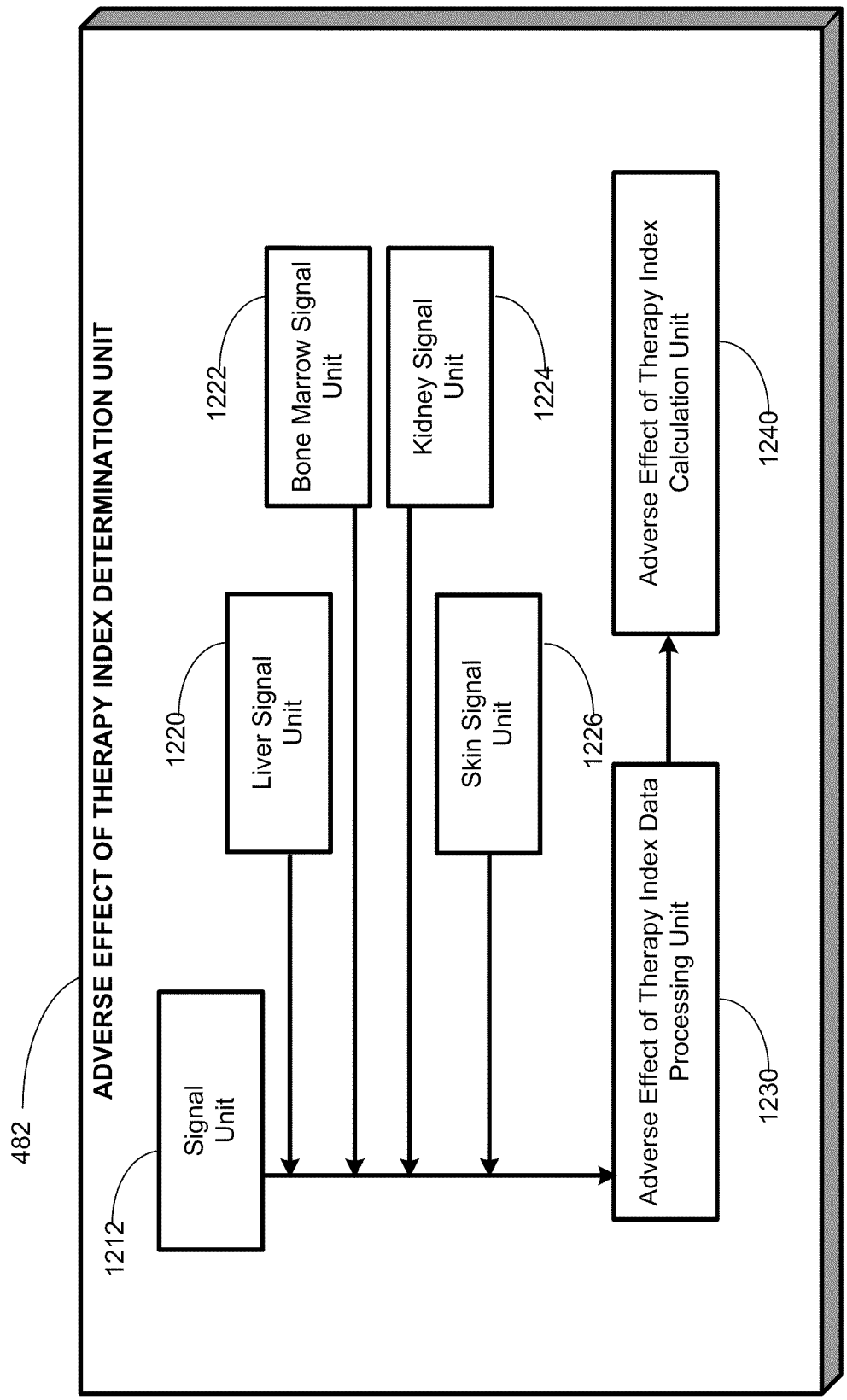
FIG. 12 is a stylized block diagram of an adverse effect of therapy index unit of a medical device or medical device system, in accordance with one illustrative embodiment of the present invention.

Turning to FIG. 12 an exemplary embodiment of an adverse effect of therapy index determination unit 482 is shown. The adverse effect of therapy index determination unit 482 can comprise at least one signal unit 1212, capable of receiving a signal as described above from which an adverse effect of therapy index can be derived. In a particular embodiment, as depicted, the adverse effect of therapy determination unit 482 can comprise one or more of a liver signal unit 1220, a bone marrow signal unit 1222, a kidney signal unit 1224, or a skin signal unit signal unit 1226.

The adverse effect of therapy index determination unit 482 can also comprise an adverse effect of therapy index data processing unit 1230. The adverse effect of therapy index data processing unit 1230 can perform any filtering, noise reduction, amplification, or other appropriate processing of the data received by the signal unit(s) 1212-1226 desired by the person of ordinary skill in the art prior to calculation of the adverse effect of therapy index.

The adverse effect of therapy index determination unit 482 can also comprise an adverse effect of therapy index calculation unit 1240. The adverse effect of therapy index calculation unit 1240 can calculate an adverse effect of therapy index from the data passed by the adverse effect of therapy index processing unit 1230.

For example, the adverse effect of therapy index calculation unit 1240 may calculate an adverse effect of therapy index as received by signal unit(s) 1212-1226 and, optionally, further processed by adverse effect of therapy index data processing unit 1230.

Figure 13:
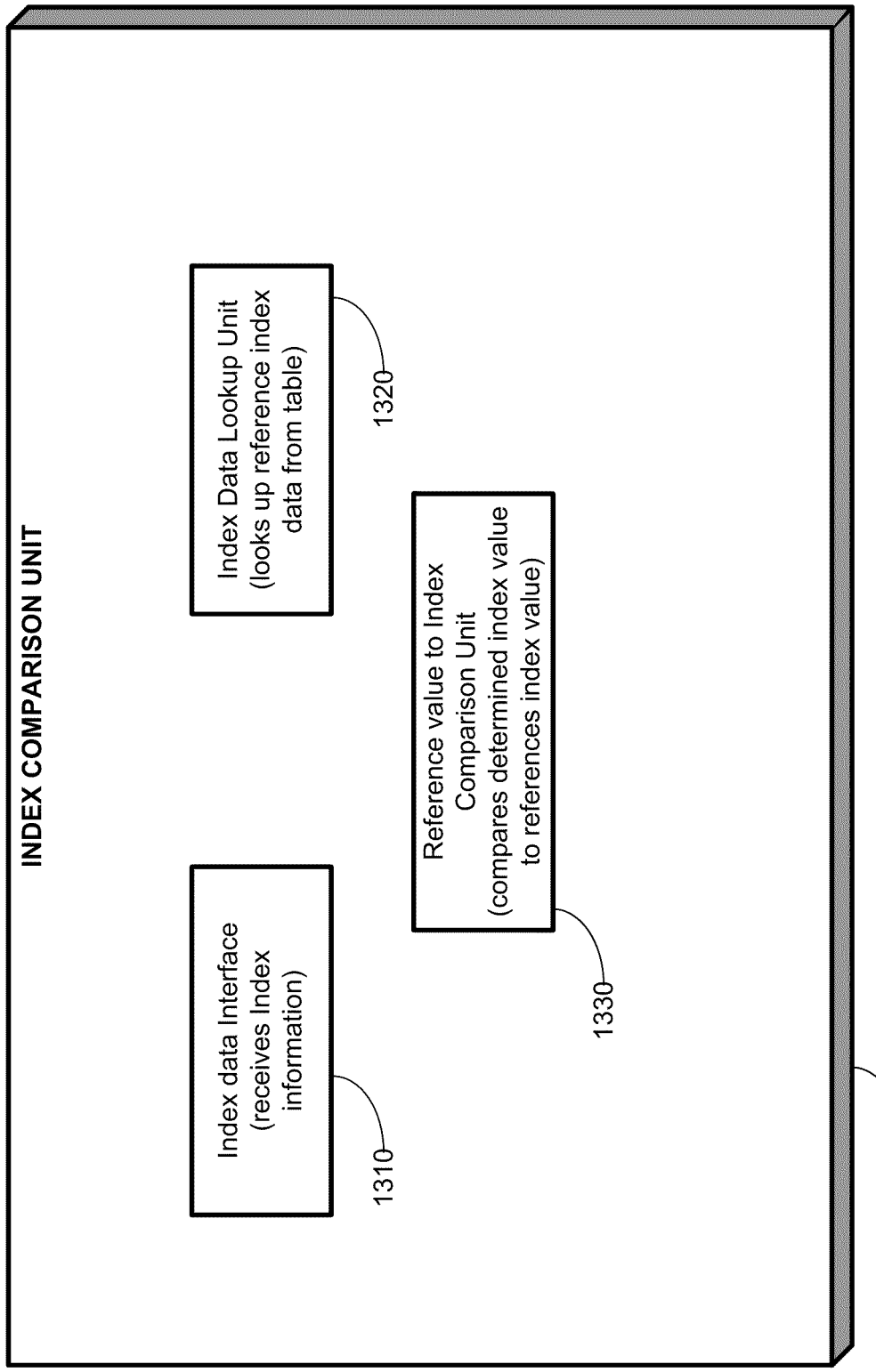
FIG. 13 is a stylized block diagram of an index comparison unit of a medical device or medical device system, in accordance with one illustrative embodiment of the present invention.

Turning to FIG. 13, a block diagram of an index comparison unit 495 is depicted. The index comparison unit 495 comprises an index data interface 1310, which receives index information from one or more of the index determination units 465, 475, 485, 477, and 479; an index data lookup unit 1320, which looks up a reference value for the index from a lookup table; and a reference value to index comparison unit 1330, which compares the determined index value from units 465-485 to the reference index value returned by index data lookup unit 1320.

Figure 14:
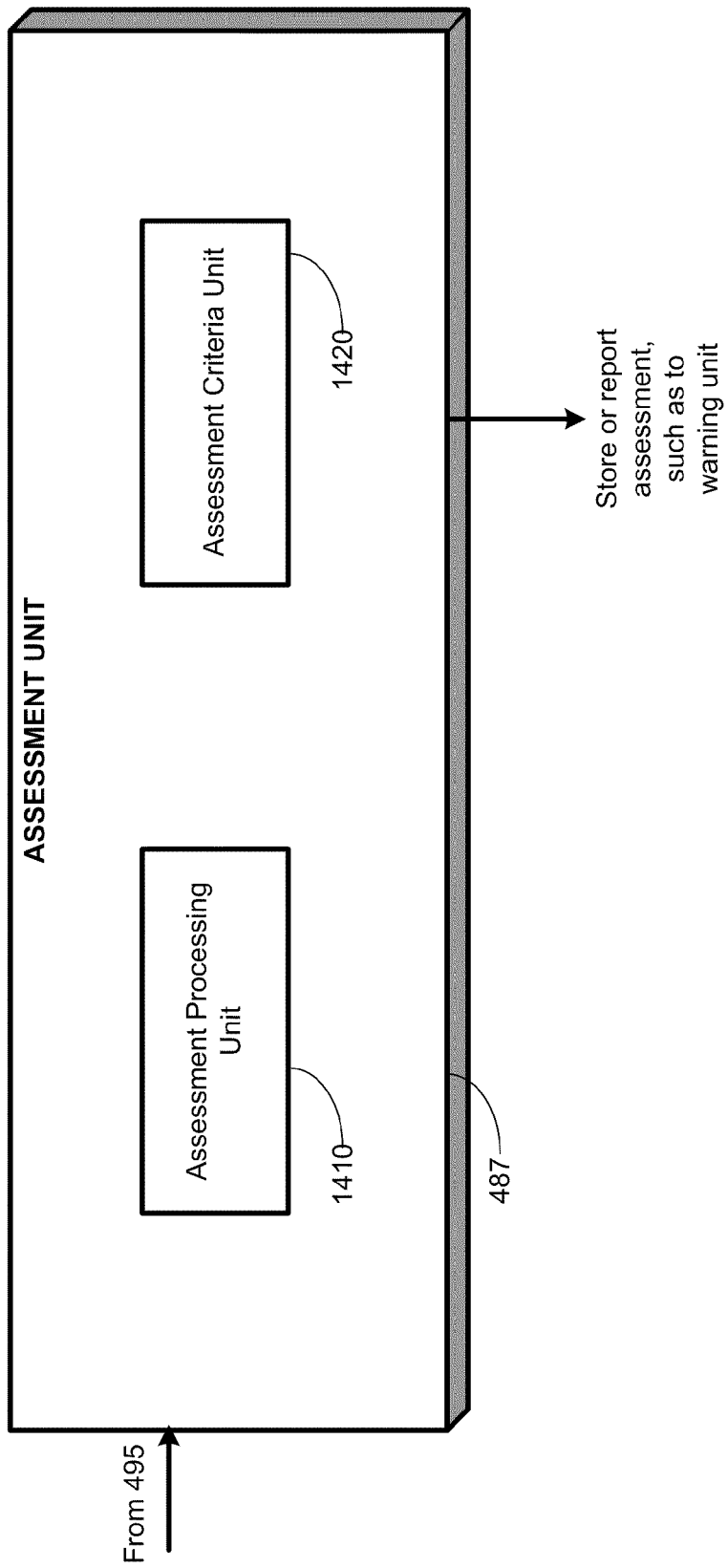
FIG. 14 is a stylized block diagram of an assessment unit of a medical device or medical device system, in accordance with one illustrative embodiment of the present invention.

Turning to FIG. 14, a block diagram of an assessment unit 487 is depicted. The assessment unit 487 receives comparison information from index comparison unit 495 and performs an assessment of at least one disease state, at least one comorbidity, or both. The assessment unit 487 contains an assessment processing unit 1410 that processes the comparison information in view of one or more stored or otherwise accessible assessment criteria returned by assessment criteria unit 1420. The assessment can be performed in real-time (without substantial delay between performing the assessment and taking any prior action referred to herein) or off-line (involving calculations making use of data stored for some length of time). The assessment processing unit 1410 yields an assessment. If the assessment unit 487 assesses a disease state, the output can comprise at least one of disease stability, disease progression, disease regression, or a finding that a disease state cannot be determined with a sufficient degree of confidence. If the assessment unit 487 assesses a state of a body system of a patient, the output can comprise at least one of body system stability, body system improvement, body system decline, or a finding that a body system of the system cannot be determined with a sufficient degree of confidence. Exemplary body systems include, but are not limited to, an autonomic system, a neurologic system, a psychiatric system, an endocrine system, a hepatic system, a bone marrow system, a renal system, and a skin system. The assessment unit 487 can then store or log its assessment in a memory, provide an output to the patient, a caregiver, or a physician, or the like. Alternatively or in addition, one or more of the indices considered in making the assessment can also be stored or logged.

In a particular embodiment, the output of the assessment can comprise quantitative data relating to the state of the disease or the body system. For example, in one embodiment, the output can comprise at least one of a magnitude of a change of a progression, a magnitude of a change of a regression, a rate of change of a progression, or a rate of change of a regression, a magnitude of a change of an improvement, a magnitude of a change of a decline, a rate of change of an improvement, or a rate of change of a decline. Alternatively or in addition, an output of an assessment of a disease state can comprise identifying new comorbidities not previously identified. These data can be used to assess the overall state of health of the subject and, when analyzed in the context of quality of life index value, provide an assessment of the patient's well being.

Regardless of its content, the output can be any form of audio, visual, or other communication. Exemplary outputs include, but are not limited to, text, graphics, video, animation, a sound tone or tones, and melodies, among others. The outputs can be sent to any device capable of presenting them to a user, such as a telephone, a handheld device, a computer, a television, or a loudspeaker, among others.

Figure 15:
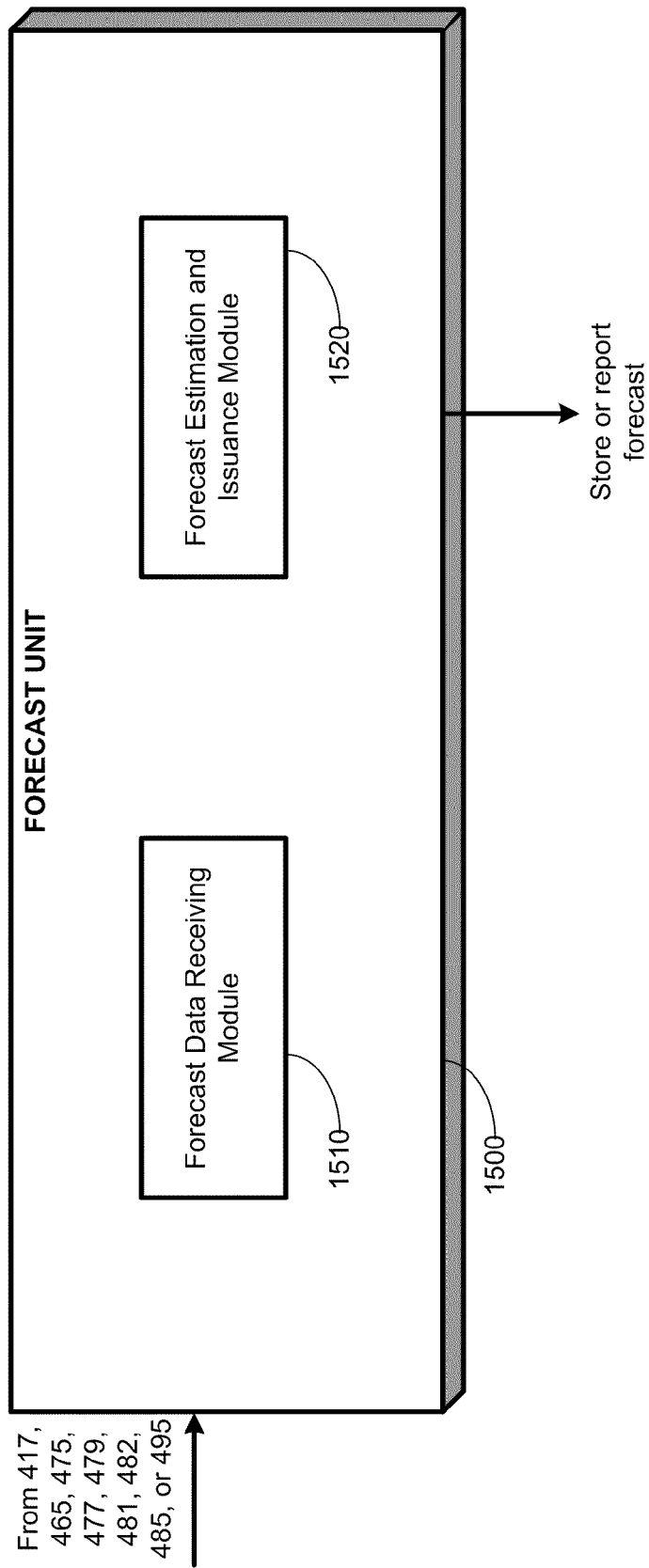
FIG. 15 is a stylized block diagram of a forecast unit of a medical device or medical device system, in accordance with one illustrative embodiment of the present invention.

Turning to FIG. 15, a block diagram of a forecast (or prognosis) unit 1500 is depicted. The forecast (or prognosis) unit comprises a forecast data receiving module 1510 capable of receiving information from one or more of the assessment unit 487, one or more index determination units 465, 475, 477, 479, or 485, one or more index comparison units 495, or a memory 417 storing prior outputs of such a unit, and forecast (or prognosis) estimation and issuance module 1520 capable of estimating from the received data a future state of the disease, wherein the forecast comprises a disease stability, a disease progression, a disease regression, and/or a state of the body system, wherein the forecast comprises a body system stability, a body system improvement, a body system decline, or a finding that no forecast can be made. In a further embodiment, wherein the forecast is of disease progression, the forecast comprises at least one of a risk of an increased magnitude of change of progression, a risk of an increased rate of change of progression, or a risk of emergence of one or more comorbidities associated with the disease. These data can be used to issue a prognosis for a state of health of patient. Forecasts or prognoses may be based on qualitative, semi-quantitative, or qualitative measures obtained using conventional forecasting methods, such as those used in the fields of geophysics, finance, population dynamics including epidemics, material sciences (e.g. predicting material fatigue), and dynamical control systems. When appropriate, clinical judgment may be applied alone or in the frame of Bayesian statistics.

In one embodiment, a medical device system is provided. The medical device system can comprise an interface to receive at least one of autonomic data, neurologic data, and quality of life data. The interface can be similar to that described above.

The medical device system can comprise at least one of an autonomic index determination unit capable of determining at least one autonomic index, a neurologic index determination capable of determining at least one neurologic index unit, or a quality of life index determination unit capable of determining at least one quality of life index. The index determination unit(s) can be similar to those described above.

The medical device system can comprise an index comparison unit capable of comparing at least one index with at least one reference value. The index comparison unit can be similar to those described above.

The medical device system can comprise a assessment unit capable of assessing a state of a disease or a body system of a patient based on at least one output of the index comparison unit. The assessment unit can be similar to those described above.

In one embodiment, the medical device system further comprises a therapy unit adapted to deliver a therapy for the disease to a patient. The therapy unit may administer therapy in a contingent ("closed-loop") manner in response to a particular manifestation of the disease, or in a non-contingent ("open-loop") manner without reference to at least one particular manifestation of the disease. A combination of contingent and non-contingent therapies may be also administered. Further, when therapy is administered in a contingent manner, a particular therapy regimen may be selected in response to particular findings output by the assessment unit. For example, if the assessment unit finds the patient's disease state is worsening, one or more therapy parameters may be modified to provide a more intensive therapy. For example, if the therapy is electrical stimulation of a neural tissue of a patient, the on-time, amplitude, and/or frequency of stimulation may be increased, and/or the off-time decreased, to provide a more intensive therapy. Therapy type (e.g., electrical, pharmacological, thermal, cognitive, etc.), and parameters including time or timing of delivery may be tailored to state variations in the probability of occurrence or severity of a manifestation of the disease.

In another embodiment, the medical device system further comprises an acute disease state detection unit adapted to detect an acute disease state in the patient. By "acute disease state" is meant a particular manifestation of the disease that is more intense or debilitating than the patient's baseline presentation. For example, if the disease is epilepsy, the "acute disease state" can be an epileptic event, such as a seizure. In this example, the acute disease state detection unit is adapted to detect an epileptic event.

In another embodiment, the medical device system further comprises a disease warning unit adapted to provide a warning signal of change in a disease state, of an impending acute disease state, or a change in a body system parameter. For example, a warning signal may be provided if there is a change in a cardiovascular index that is deemed serious, exceeds a predetermined value, or if there is an impending seizure. This warning signal may be delivered to the subject, a caregiver, or to an emergency medical unit.

In one embodiment, the warning signal is proportional to at least one of a magnitude of a change of a disease progression, a rate of change of a disease progression, or a correlation of the index value to life span (deterioration in an autonomic cardiac parameter is more likely to negatively impact life span than in a neurologic index, such as cognitive decline). Alternatively or in addition, in one embodiment, the warning signal is proportional to at least one of a magnitude of a change of a body system decline or a rate of change of a body system decline. For example, the warning signal may comprise a tone characterized by a pitch and/or a volume, and the warning signal may become higher in pitch and/or louder in proportion to a magnitude or rate of change of a disease state or a body system decline.

In addition to components of the medical device 400 described above, an implantable medical system may comprise a storage unit to store an indication of at least one of seizure or an increased risk of a seizure. The storage unit may be the memory 417 of the medical device 400, another storage unit of the medical device 400, or an external database, such as the local database unit 455 or a remote database unit 450. The storage unit can allow retention of a history of index values and/or assessments of disease state and/or comorbidity. For example, the output from this storage unit can be sent to the assessment unit 487 to quantify disease state and determine if there is progression, stabilization, or regression of the disease, or if a determination cannot be made. Alternatively or in addition, the output from this storage unit can be sent to the assessment unit 487 to quantify a state of a body system of a patient. The medical device 400 may communicate the indication via the communications unit 460. Alternatively or in addition to an external database, the medical device 400 may be adapted to communicate the indication to at least one of a patient, a caregiver, or a healthcare provider.

In various embodiments, one or more of the units or modules described above may be located in a monitoring unit 470 or a remote device 492, with communications between that unit or module and a unit or module located in the medical device 400 taking place via communication unit 460. For example, in one embodiment, one or more of the interface, the autonomic index determination unit 465, the neurologic index determination unit 475, the stress marker index determination unit 477, the psychiatric index determination unit 479, an endocrine index determination unit 481, an adverse effect of therapy index determination unit 482, a physical fitness index determination unit 483, the quality of life index determination unit 485, the index comparison unit 495, and/or the assessment unit 487 may be external to the medical device 400, e.g., in a monitoring unit 470. Locating one or more of the foregoing units outside the medical device 400 may be advantageous if the calculation(s) is/are computationally intensive, in order to reduce energy expenditure and heat generation in the medical device 400 or to expedite calculation.

The monitoring unit 470 may be a device that is capable of transmitting and receiving data to and from the medical device 400. In one embodiment, the monitoring unit 470 is a computer system capable of executing a data-acquisition program. The monitoring unit 470 may be controlled by a healthcare provider, such as a physician, at a base station in, for example, a doctor's office. In alternative embodiments, the monitoring unit 470 may be controlled by a patient in a system providing less interactive communication with the medical device 400 than another monitoring unit 470 controlled by a healthcare provider. Whether controlled by the patient or by a healthcare provider, the monitoring unit 470 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 470 may download various parameters and program software into the medical device 400 for programming the operation of the medical device, and may also receive and upload various status conditions and other data from the medical device 400. Communications between the monitoring unit 470 and the communication unit 460 in the medical device 400 may occur via a wireless or other type of communication, represented generally by line 477 in FIG. 4. This may occur using, e.g., wand 355 (FIG. 3) to communicate by RF energy with an implantable signal generator 310. Alternatively, the wand may be omitted in some systems, e.g., systems in which the MD 400 is non-implantable, or implantable systems in which monitoring unit 470 and MD 400 operate in the MICS bandwidths.

In one embodiment, the monitoring unit 470 may comprise a local database unit 455. Optionally or alternatively, the monitoring unit 470 may also be coupled to a database unit 450, which may be separate from monitoring unit 470 (e.g., a centralized database wirelessly linked to a handheld monitoring unit 470). The database unit 450 and/or the local database unit 455 are capable of storing various patient data. These data may comprise patient parameter data acquired from a patient's body, therapy parameter data, seizure severity data, therapeutic efficacy data, and/or disease state assessment data. The database unit 450 and/or the local database unit 455 may comprise data for a plurality of patients, and may be organized and stored in a variety of manners, such as in date format, severity of disease format, etc. The database unit 450 and/or the local database unit 455 may be relational databases in one embodiment. A physician may perform various patient management functions (e.g., programming parameters for a responsive therapy and/or setting thresholds for one or more detection parameters) using the monitoring unit 470, which may include obtaining and/or analyzing data from the medical device 400 and/or data from the database unit 450 and/or the local database unit 455. The database unit 450 and/or the local database unit 455 may store various patient data.

One or more of the blocks illustrated in the block diagrams of the medical device 400 in FIGS. 4-12 may comprise hardware units, software units, firmware units, or any combination thereof. Additionally, one or more blocks illustrated in FIGS. 4-12 may be combined with other blocks, which may represent circuit hardware units, software algorithms, etc. Additionally, any number of the circuitry or software units associated with the various blocks illustrated in FIGS. 4-12 may be combined into a programmable device, such as a field programmable gate array (FPGA), an ASIC device, etc.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Although not so limited, in one embodiment, the method further comprises applying a therapy to a neural tissue of the patient, in response to the assessing. In a further embodiment, the therapy is an electrical therapy. In a further embodiment, the neural tissue is a cranial nerve, such as the vagus nerve.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to a neural structure in the patient's body. The signal is an exogenous signal that is distinct from the endogenous electro-chemical, activity inherent to the patient's body and the environment. In other words, the stimulation signal (whether electrical, mechanical, magnetic, electro-magnetic, photonic, acoustic, cognitive, and/or chemical in nature) applied to a cranial nerve or to other nervous tissue structure in the present invention is a signal applied from a medical device, e.g., a neurostimulator. Alternatively or in addition, electrochemical activity inherent to the patient's body or brain may be tapped, harnessed or modified (as in the case of cognitive therapy) to treat a disease manifestation or the disease itself.

A "therapeutic signal" refers to a stimulation signal delivered to a patient's body with the intent of treating a medical condition through a suppressing (blocking) or modulating effect to neural tissue. The effect of a stimulation signal on neuronal activity may be suppressing or modulating; however, for simplicity, the terms "stimulating", suppressing and modulating, and variants thereof, are sometimes used interchangeably herein. In general, however, the delivery of an exogenous signal itself refers to "stimulation" of the neural structure, while the effects of that signal, if any, on the electrical activity of the neural structure are properly referred to as suppression or modulation.

Depending upon myriad factors such as the history (recent and distant) of the nervous system, stimulation parameters and time of day, to name a few, the effects of stimulation upon the neural tissue may be excitatory or inhibitory, facilitatory or disfacilitatory and may suppress, enhance or leave unaltered, neuronal activity. One can witness a suppressing effect when, for example, a stimulation signal applied to neural tissue prevents or ameliorates abnormal neurological activity (e.g., epileptic seizures). This suppressing effect takes place through multiple mechanisms, as described in the foregeoing articles. Suppression of abnormal neural activity is a threshold or suprathreshold process and the temporal scale over which it may occur is usually on the order of tens or hundreds of milliseconds. Modulation of abnormal or undesirable neural activity, unlike suppression is a "sub-threshold" process in the spatio-temporal domain that may summate and result under certain conditions, in threshold or suprathreshold neural events. The temporal scale of modulation is much longer than that of suppression, encompassing seconds to months or even years. In addition to inhibition or dysfacilitation, modification of neural activity may occur by wave annihilation (a concept borrowed from wave mechanics) or through phase resetting.

Electrotherapy may be provided by implanting an electrical device, i.e., an implantable medical device (IMD), inside a patient's body stimulation of a nervous tissue, such as a cranial nerve. Generally, electrotherapy signals that suppress or modulate neural activity are delivered by the IMD via one or more leads or wirelessly. When applicable, the leads generally terminate at their distal ends in one or more electrodes, and the electrodes, in turn, are coupled to tissue in the patient's body. For example, a number of electrodes may be attached to various points of a nerve or other tissue inside a human body for delivery of a neurostimulation signal.

While contingent (also referred to as "closed-loop," "active," or "feedback" stimulation (i.e., electrotherapy applied in response to sensed information, such as heart rate)) stimulation schemes have been proposed, non-contingent, programmed periodic stimulation is the prevailing modality. For example, vagus nerve stimulation for the treatment of epilepsy usually involves a series of grouped electrical pulses defined by an "on-time" (such as 30 sec) and an "off-time" (such as 5 min). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the combination of the on-time and off-time, and which describes the percentage of time that the electrical signal is applied to the nerve.

In open-loop VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in open-loop VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in VNS may be programmed over a range of values. The pulse width for the pulses in a pulse burst of open-loop VNS may be set to a value not greater than about 1 msec, such as about 250-500 μsec, and the number of pulses in a pulse burst is typically set by programming a frequency in a range of about 20-300 Hz (i.e., 20 pulses per second to 300 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Returning to systems for providing cranial nerve stimulation, such as that shown in FIG. 3, and as stated above, alternatively or in addition to a responsive treatment, if any, cranial nerve stimulation may be provided on a continuous basis to alleviate chronic aspects of the patient's medical disorder. Where cranial nerve stimulation is provided based solely on programmed off-times and on-times, the stimulation may be referred to as passive, inactive, open-loop, non-feedback, or non-contingent stimulation. In contrast, stimulation may be triggered by one or more feedback loops according to changes in the body or brain of the patient. This stimulation may be referred to as active, closed-loop, feedback-loop, or contingent stimulation. In one embodiment, feedback-loop stimulation may be manually-triggered stimulation, in which the patient manually causes the activation of a pulse burst outside of the programmed on-time/off-time cycle at a time of the patient's choosing, for example, in response to a sensation of an impending seizure. The patient may manually activate an implantable signal generator 310 to stimulate the cranial nerve, such as vagus nerve 327, to treat an acute episode of a medical condition, e.g., a seizure. The patient may also be permitted to alter the intensity of the signals applied to the cranial nerve within limits established by the physician.

Patient activation of a medical device 300 may involve use of an external control magnet for operating a reed switch in an implanted device, for example. Certain other techniques of manual and automatic activation of implantable medical devices are disclosed in U.S. Pat. No. 5,304,206 to Baker, Jr., et al. ("the '206 patent"). According to the '206 patent, means for manually activating or deactivating the electrical signal generator 310 may include a sensor such as piezoelectric element mounted to the inner surface of the generator case and adapted to detect light taps by the patient on the implant site. One or more taps applied in fast sequence to the skin above the location of the electrical signal generator 310 in the patient's body may be programmed into the implanted medical device 300 as a signal for intensification of the electrical signal. Two taps spaced apart by a slightly longer duration of time may be programmed into the medical device 300 to indicate a desire to de-intensify the electrical signal. The patient may be given limited control over operation of the device to an extent which may be determined by the program or entered by the attending physician. The patient may also activate the medical device 300 using other suitable techniques or apparatus.

In one embodiment, the medical device 400 may also be capable of detecting a manual input from the patient. The manual input may include a magnetic signal input, a tap input, a wireless data input to the medical device 400, etc.

The above methods may be performed by a computer readable program storage device encoded with instructions that, when executed by a computer, perform the method described herein.

Figure 16:
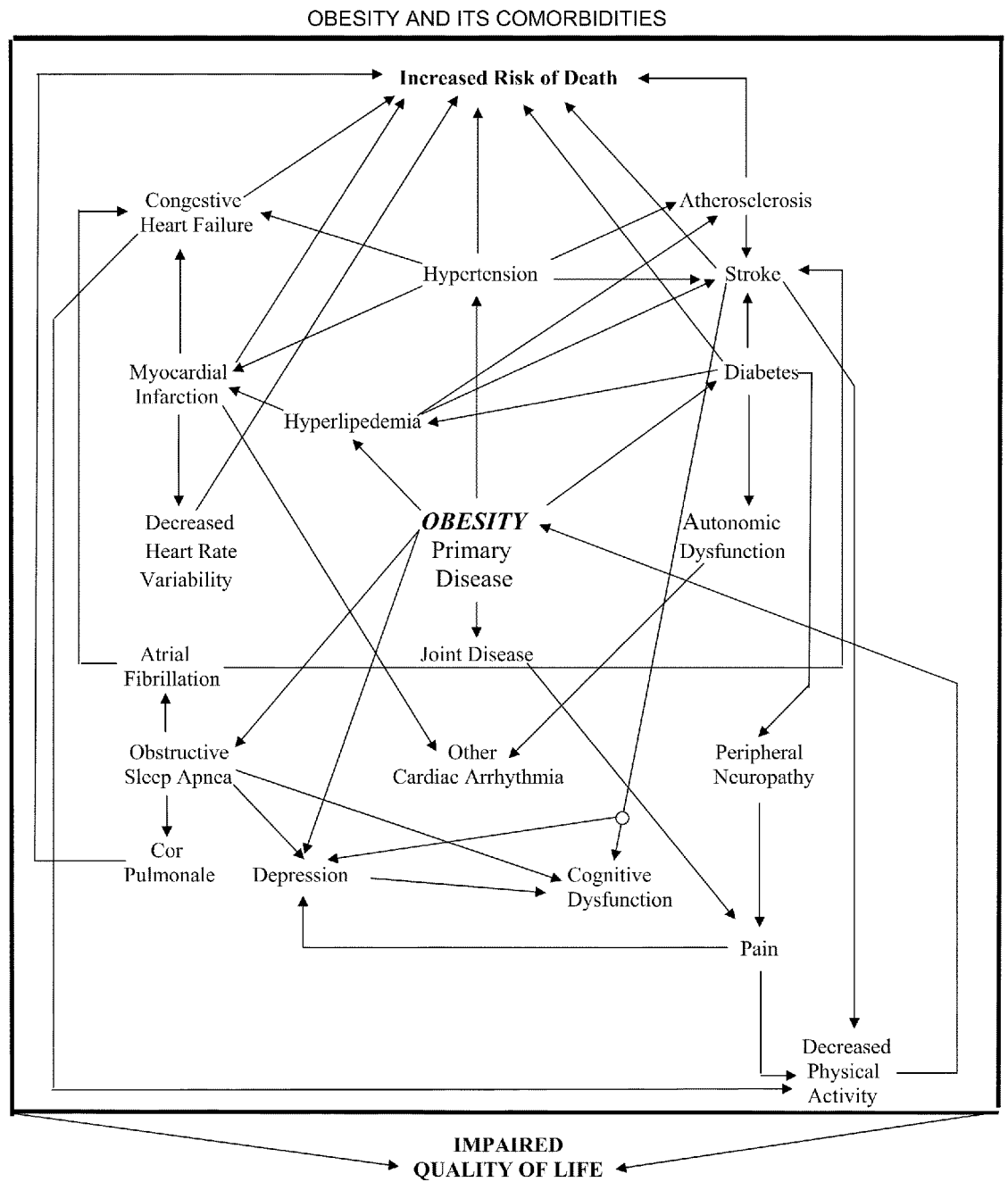
FIG. 16 is a stylized diagram of relationships between obesity and some of its comorbidities, with the direction of an arrow showing a source's tendency to increase or make more likely a target.

In one embodiment, the disease is obesity. As depicted in FIG. 16, with the directionality of each arrow indicating an amplifying effect, obesity substantially increases the patient's risk of developing diabetes mellitus, arterial hypertension, hyperlipidemia and obstructive sleep apnea, while shortening life span and degrading quality of life. Arterial hypertension, diabetes and hyperlipidemia, in turn, accelerate atherosclerosis, further increasing the risks for myocardial infarction, stroke, congestive heart failure, and avascular gangrene. Similarly, obstructive sleep apnea causes intractable arterial hypertension, atrial fibrillation, cognitive deterioration, depression, sexual dysfunction, and chronic headaches.

Figure 17:
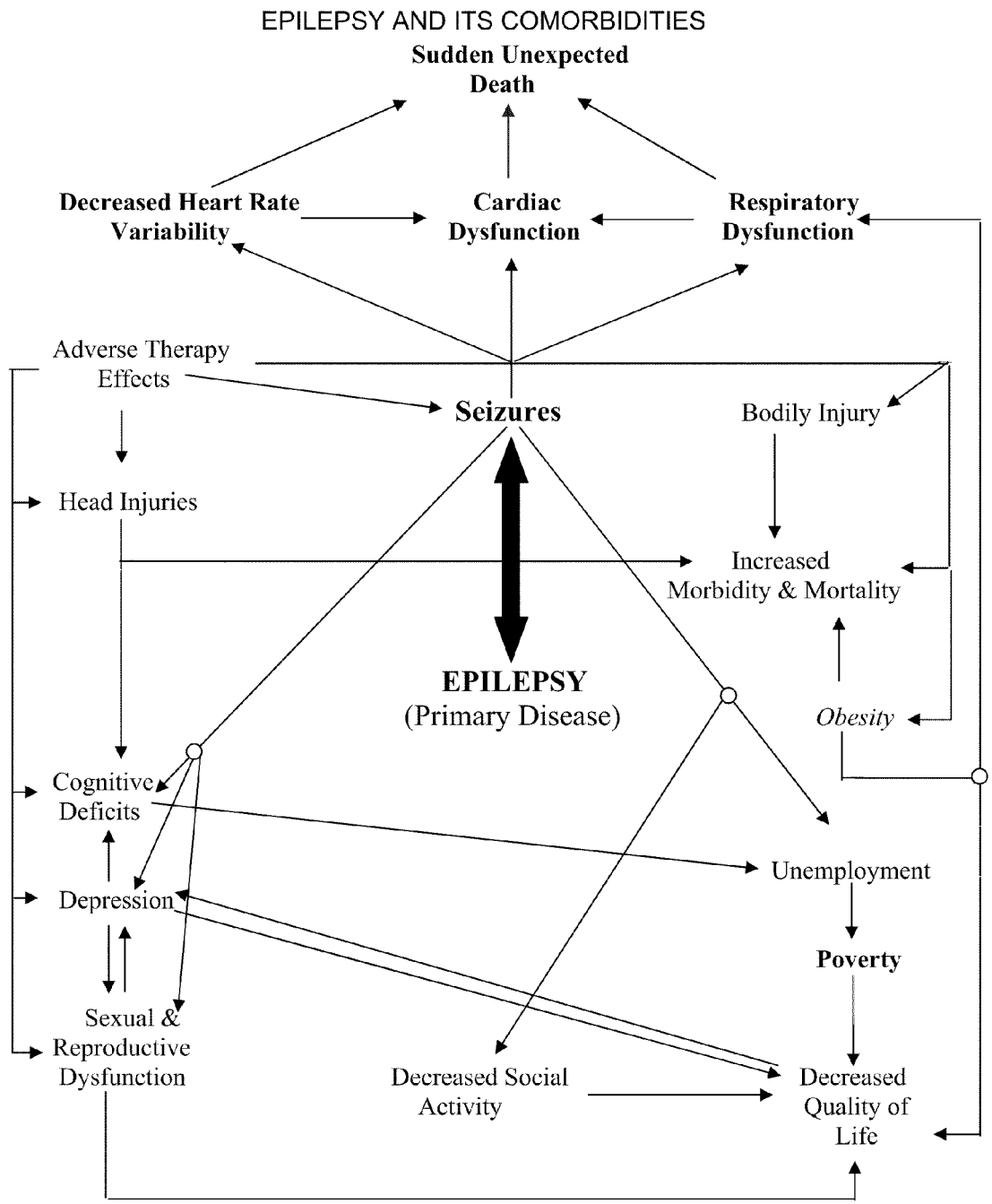
FIG. 17 is a stylized diagram of relationships between epilepsy and some of its comorbidities, with the direction of an arrow showing a source's tendency to increase or make more likely a target.

In one embodiment, the disease is epilepsy. Pharmacoresistant seizures are associated with an increase in mortality and morbidity rates (compared to the general population and to epileptics whose seizures are controlled by medications), eventual impairment of cognitive functions and mental health, and markedly degraded quality of life for patients and their families. Seizures may impair motor control, responsiveness to a wide class of stimuli, and other cognitive functions. Certain pharmacological agents used for treatment of epilepsy cause osteoporosis, reproductive dysfunction, liver and bone marrow damage, and in rare cases, death. FIG. 17 depicts relationships between epilepsy and some of its comorbidities, with the directionality of each arrow indicating an amplifying effect.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

In various embodiments, the present invention relates to the subject matter of the following numbered paragraphs:

1. A medical device system, comprising:
at least one of an autonomic index determination unit capable of determining at least one autonomic index, a neurologic index determination unit capable of determining at least one neurologic index, a stress marker index determination unit capable of determining at least one stress marker index, a psychiatric index determination unit capable of determining at least one psychiatric index, an endocrine index determination unit capable of determining at least one endocrine index, an adverse effect of therapy index determination unit capable of determining at least one adverse effect of therapy index, a physical fitness index determination unit capable of determining at least one physical fitness index, or a quality of life index determination unit capable of determining at least one quality of life index;
an index comparison unit capable of comparing at least one index with at least one reference value;
a body system state assessment unit capable of assessing a state of a body system of a patient, wherein the body system comprises at least one of an autonomic system, a neurologic system, a psychiatric system, an endocrine system, an hepatic system, a renal system, a bone marrow system, a skin system, or subsystems of the foregoing; and
an output unit capable of providing an output relating to the assessment, wherein the output comprises at least one of body system stability, body system improvement, body system decline, or a finding that a state of the body system cannot be determined.

2. The medical device system of numbered paragraph 1, further comprising a disease state assessment unit capable of assessing a state of a disease, wherein the output comprises disease stability, disease progression, disease regression, or a finding that a disease state cannot be determined.

3. The medical device system of numbered paragraph 2, further comprising: a comorbidity identification unit adapted to identify a comorbidity associated with the disease.

4. The medical device system of numbered paragraph 1, further comprising:
at least one interface capable of receiving at least one of an autonomic signal, a neurologic signal, a stress marker signal, a psychiatric signal, an endocrine signal, an adverse effect of therapy signal, a physical fitness signal, or a quality of life signal of a patient.

5. The medical device system of numbered paragraph 1, further comprising:
a forecast unit capable of forecasting a state of the body system, wherein the forecast comprises a body system stability, a body system improvement, a body system decline, or a finding that no forecast can be made.

6. The medical device system of numbered paragraph 1, further comprising:
a logging unit capable of logging one or more of the assessments or indices.

7. The medical device system of numbered paragraph 1, wherein the autonomic index determination unit comprises at least one of:
a cardiovascular indication processing unit,
a respiration indication processing unit,
a blood parameter indication processing unit,
a pupillary response indication processing unit,
a body temperature indication processing unit, or
a skin resistance indication processing unit; and
the neurologic index determination unit comprises at least one of:
an attention aptitude indication processing unit,
a responsiveness indication processing unit,
a memory indication processing unit,
a kinetic indication processing unit, or
a cognitive aptitude indication processing unit; and
the stress marker index determination unit comprises at least one of:
a cortisol parameter indication processing unit, or
a catecholamine parameter indication processing unit.

8. A medical device system, comprising:
an autonomic index determination unit capable of determining at least one autonomic index;
a neurologic index determination unit capable of determining at least one neurologic index;
an index comparison unit capable of comparing the at least one autonomic index with at least one first reference value and the at least one neurologic index with at least one second reference value;
an epilepsy disease state assessment unit capable of assessing a state of an epilepsy disease; and an output unit capable of providing an output relating to the assessment, wherein the output comprises at least one of disease stability, disease progression, disease regression, or a finding that a disease state cannot be determined 9. The medical device system of numbered paragraph 8, further comprising:
a warning unit adapted to provide a warning if the epilepsy disease state assessment unit yields an assessment of disease progression.

10. The medical device system of numbered paragraph 8, further comprising:
a therapy unit adapted to deliver a therapy for epilepsy to a patient.

11. The medical device system of numbered paragraph 8, further comprising:
at least one interface capable of receiving at least one of autonomic data or neurologic data.

12. The medical device system of numbered paragraph 8, further comprising:
a forecast unit capable of forecasting a state of the disease, wherein the forecast comprises a disease stability, a disease progression, a disease regression, or a finding that no forecast can be made.

13. The medical device system of numbered paragraph 8, further comprising:
a logging unit capable of logging one or more of the assessments or indices.

14. The medical device system of numbered paragraph 8, wherein the autonomic index determination unit comprises at least one of:
a cardiovascular indication processing unit,
a respiration indication processing unit,
a blood parameter indication processing unit,
a pupillary response indication processing unit,
a body temperature indication processing unit, or
a skin resistance indication processing unit; and
the neurologic index determination unit comprises at least one of:
an attention aptitude indication processing unit,
a responsiveness indication processing unit,
a memory indication processing unit,
a kinetic indication processing unit, or
a cognitive aptitude indication processing unit.

15. The medical device system of numbered paragraph 8, further comprising:
a comorbidity identification unit adapted to identify a comorbidity associated with the disease.

17. A medical device system, comprising:
at least one assessment unit capable of assessing at least one of a patient's disease state, a quality of life, or a physical fitness,
at least one determination unit capable of determining at least one of a disease state assessment, a quality of life assessment, or a physical fitness assessment;
at least one comparison unit capable of comparing the at least one disease state assessment, quality of life assessment, or physical fitness assessment to at least one reference value,
a disease state assessment unit capable of assessing at least one of disease state, quality of life, or physical fitness; and
an output unit capable of providing an output relating to an assessment of the patient's health, wherein the output comprises disease stability, disease progression, disease regression, or a finding that a disease state cannot be determined 101. A computer readable program storage unit encoded with instructions that, when executed by a computer, perform a method for assessing a primary disease state and a body system impacted by the primary disease, comprising:

receiving at least a first index and a second index, each index relating to at least one of an autonomic index, a neurologic index, a stress marker index, a psychiatric index, an endocrine index, an adverse effect of therapy index, a physical fitness index, or a quality of life index of a patient,
comparing the at least one first index to at least one first reference value associated with the at least one first index;
comparing the at least one second index to at least one second reference value associated with the at least one second index;
assessing a state of said primary disease of the patient based on the comparing;
assessing a state of a body system of the patient based on the assessing the state of the disease, wherein the body system comprises at least one of an autonomic system, a neurologic system, a psychiatric system, an endocrine system, a hepatic system, a renal system, a bone marrow system, a skin system, or subsystems of the foregoing; and
providing an output relating to the assessment of the state of the primary disease and the assessment of the state of the body system, wherein the output comprises at least one of disease stability, disease progression, disease regression, or a finding that a disease state cannot be determined, and the output further comprises at least one of body system stability, body system improvement, body system decline, or a finding that a state of the body system cannot be determined 102. The computer readable program storage unit of numbered paragraph 101, wherein the method further comprises:
assessing a state of a second disease of the patient based on the comparing, wherein the output further comprises at least one of disease stability, disease progression, disease regression, or a finding that a disease state cannot be determined; and
assessing a state of a second body system of the patient based on the comparing, wherein the body system comprises at least one of an autonomic system, a neurologic system, a psychiatric system, an endocrine system, a hepatic system, a renal system, a bone marrow system, a skin system, or subsystems of the foregoing, and the output further comprises at least one of body system stability, body system improvement, body system decline, or a finding that a state of the body system cannot be determined 103. The computer readable program storage unit of numbered paragraph 101, wherein the output comprises at least one of a magnitude of a change of a progression, a magnitude of a change of a regression, a rate of change of a progression, or a rate of change of a regression, a magnitude of a change of an improvement, a magnitude of a change of a regression, a rate of change of an improvement, or a rate of change of a regression.

104. The computer readable program storage unit of numbered paragraph 101, wherein the at least one first index is at least one autonomic index and the at least one second index is at least one neurologic index.

105. The computer readable program storage unit of numbered paragraph 104, wherein the at least one autonomic index comprises a cardiovascular parameter, a respiration parameter, a body temperature parameter, a skin resistance parameter, or two or more thereof; and
the at least one neurologic index comprises an attention aptitude parameter, a responsiveness parameter, a memory parameter, a kinetic parameter, a cognitive aptitude parameter, or two or more thereof 106. The computer readable program storage unit of numbered paragraph 101, wherein the disease is epilepsy.

107. The computer readable program storage unit of numbered paragraph 101, wherein the method further comprises providing a warning signal to the patient, a physician, or a caregiver if assessing indicates at least one of disease progression or body system decline.

108. The computer readable program storage unit of numbered paragraph 107, wherein the warning signal is proportional to at least one of a magnitude of a change of a progression, a rate of change of a progression, a magnitude of a change of a body system decline, or a rate of change of a body system decline.

109. The computer readable program storage unit of numbered paragraph 101, wherein the first index comprises a weighted composite of a first plurality of autonomic indices, neurologic indices, stress marker indices, psychiatric indices, endocrine indices, adverse effect of therapy indices, physical fitness indices, quality of life indices, or two or more thereof;
the second index comprises a weighted composite of a second plurality of autonomic indices, neurologic indices, stress marker indices, psychiatric indices, endocrine indices, adverse effect of therapy indices, physical fitness indices, quality of life indices, or two or more thereof;
or both.

110. The computer readable program storage unit of numbered paragraph 101, wherein at least one of the first reference value or the second reference value is based on the patient's history or on normative data.

111. The computer readable program storage unit of numbered paragraph 101, wherein at least one of the first index or the second index comprises a measure of central tendency, a measure of dimensionality, a measure of fractality, a measure of stationarity, a measure of long-range dependency, a measure of clustering, a distribution of measures of central tendency, a distribution of measures of dimensionality, a distribution of measures of fractality, a distribution of measures of stationarity, a distribution of measures of long-range dependency, a distribution of measures of clustering, or two or more thereof 112. The computer readable program storage unit of numbered paragraph 101, wherein the method further comprises forecasting a state of the disease, wherein the forecast comprises a disease stability, a disease progression, a disease regression, or a finding that no forecast can be made.

113. The computer readable program storage unit of numbered paragraph 112, wherein the forecast is of disease progression and the forecast comprises at least one of a risk of an increased magnitude of change of progression, a risk of an increased rate of change of progression, or a risk of emergence of one or more comorbidities associated with the disease.

114. The computer readable program storage unit of numbered paragraph 101, wherein the method further comprises forecasting a state of the body system, wherein the forecast comprises a body system stability, a body system improvement, a body system decline, or a finding that no forecast can be made.

115. The computer readable program storage unit of numbered paragraph 101, wherein the assessment of the state of the disease comprises identifying one or more comorbidities associated with the disease.

116. A computer readable program storage unit encoded with instructions that, when executed by a computer, perform a method for assessing a patient's health, comprising:
receiving at least one assessment of at least one of a patient's disease state, a quality of life, or a physical fitness,
comparing the at least one assessment to at least one reference value associated with at least one previous assessment from the patient or with normative data,
assessing at least one of disease state, quality of life, or physical fitness based on the comparing; and
providing an output relating to an assessment of the patient's health, wherein the output comprises at least one of disease state stability, disease state progression, disease state regression, a finding that the disease state cannot be determined, quality of life stability, quality of life improvement, quality of life decline, a finding that the quality of life cannot be determined, physical fitness stability, physical fitness improvement, physical fitness decline, or a finding that physical fitness cannot be determined.

201. A medical device system, comprising:
at least one of an autonomic index determination unit capable of determining at least one autonomic index, a neurologic index determination unit capable of determining at least one neurologic index, a stress marker index determination unit capable of determining at least one stress marker index, a psychiatric index determination unit capable of determining at least one psychiatric index, an endocrine index determination unit capable of determining at least one endocrine index, an adverse effect of therapy index determination unit capable of determining at least one adverse effect of therapy index, a physical fitness index determination unit capable of determining at least one physical fitness index, or a quality of life index determination unit capable of determining at least one quality of life index;
an index comparison unit capable of comparing at least one first index with at least one first reference value associated with the at least one first index and comparing at least one second index with at least one second reference value associated with the at least one second index;
a body system state assessment unit capable of assessing a state of a body system of a patient, wherein the body system comprises at least one of an autonomic system, a neurologic system, a psychiatric system, an endocrine system, a hepatic system, a renal system, a bone marrow system, a skin system, or subsystems of the foregoing;
a disease state assessment unit capable of assessing a state of a disease; and
an output unit capable of providing an output relating to the assessment, wherein the output comprises at least one of body system stability, body system improvement, body system decline, or a finding that a state of the body system cannot be determined, and the output further comprises disease stability, disease progression, disease regression, or a finding that a disease state cannot be determined 202. The medical device system of numbered paragraph 201, further comprising:
at least one interface capable of receiving at least one of an autonomic index, a neurologic index, a stress marker index, a psychiatric index, an endocrine index, an adverse effect of therapy index, a physical fitness index, or a quality of life index of a patient.

203. The medical device system of numbered paragraph 201, further comprising:
a forecast unit capable of forecasting at least one of a state of the disease or a state of the body system, wherein the forecast comprises a disease stability, a disease progression, a disease regression, a body system stability, a body system improvement, a body system decline, or a finding that no forecast can be made.

204. The medical device system of numbered paragraph 201, further comprising:
a logging unit capable of logging one or more of the assessments or indices.

205. The medical device system of numbered paragraph 201, wherein the autonomic index determination unit comprises at least one of:
- a cardiovascular indication processing unit,
- a respiration indication processing unit,
- a blood parameter indication processing unit,
- a pupillary response indication processing unit,
- a body temperature indication processing unit, or
- a skin resistance indication processing unit; and the neurologic index determination unit comprises at least one of:
- an attention aptitude indication processing unit,
- a responsiveness indication processing unit,
- a memory indication processing unit,
- a kinetic indication processing unit, or
- a cognitive aptitude indication processing unit; and the stress marker index determination unit comprises at least one of:
- a cortisol parameter indication processing unit, or
- a catecholamine parameter indication processing unit.

206. The medical device system of numbered paragraph 201, further comprising:
- a comorbidity identification unit adapted to identify a comorbidity associated with the disease.

207. A medical device system, comprising:
at least one of an autonomic index determination unit capable of determining at least one of a cardiovascular parameter, a respiratory parameter, or an autonomic parameter of a patient; or a neurologic index determination unit capable of determining at least one of a responsiveness parameter or a kinetic parameter of the patient;
an index comparison unit capable of comparing the cardiovascular parameter with at least one first reference value, the respiratory parameter with at least one second reference value, and the kinetic parameter with at least one third reference value;
a real-time body system state assessment unit capable of assessing in real-time a state of a body system of the patient, wherein the body system comprises at least one of an autonomic system, a neurologic system, a psychiatric system, an endocrine system, a hepatic system, a renal system, a bone marrow system, a skin system, or subsystems of the foregoing;
a communication unit capable of sending at least one of the real-time assessment, the at least one autonomic parameter, or the at least one neurologic parameter to an off-line body system state assessment unit;
an off-line body system state assessment unit capable of (a) receiving the at least one of the real-time assessment, the at least one autonomic parameter, or the at least one neurologic parameter; (b) receiving at least one second index comprising at least one of an autonomic index, a neurologic index, a stress marker index, a psychiatric index, an endocrine index, an adverse effect of therapy index, a physical fitness index, or a quality of life index of a patient; and (c) assessing off-line a state of a body system of the patient, wherein the body system comprises at least one of an autonomic system, a neurologic system, a psychiatric system, an endocrine system, a hepatic system, a renal system, a bone marrow system, a skin system, or subsystems of the foregoing; and
an output unit capable of providing an output relating to at least one of the real-time assessment or the off-line assessment, wherein the output relating to the real-time assessment comprises at least one of body system stability, body system improvement, body system decline, or a finding that a state of the body system cannot be determined, and the output relating to the off-line assessment comprises at least one of body system stability, body system improvement, body system decline, or a finding that a state of the body system cannot be determined.

208. The medical device system of numbered paragraph 207, wherein the communication unit is further capable of providing a warning signal to the patient, a physician, or a caregiver if assessing in real-time indicates body system decline.

209. The medical device system of numbered paragraph 208, wherein the warning signal is proportional to at least one of a magnitude of a change in body system decline or a rate of change in body system decline.

210. The medical device system of numbered paragraph 208, further comprising a storage unit capable of storing at least one of the real-time assessment, the off-line assessment, the at least one autonomic index, the at least neurologic index, or the at least one second index.

211. A medical device system, comprising:
at least one assessment unit capable of assessing at least one of a patient's disease state, a quality of life, or a physical fitness,
at least one determination unit capable of determining at least one of a disease state assessment, a quality of life assessment, or a physical fitness assessment;
at least one comparison unit capable of comparing the at least one disease state assessment, quality of life assessment, or physical fitness assessment to at least one reference value,
a disease state assessment unit capable of assessing at least one of disease state, quality of life, or physical fitness; and
an output unit capable of providing an output relating to an assessment of the patient's health, wherein the output comprises disease state stability, disease state progression, disease state regression, a finding that the disease state cannot be determined, quality of life stability, quality of life improvement, quality of life decline, a finding that the quality of life cannot be determined, physical fitness stability, physical fitness improvement, physical fitness decline, or a finding that physical fitness cannot be determined.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

The invention claimed is:

1. A non-transitory computer readable program storage unit encoded with instructions that, when executed by a computer, perform a method for assessing an epilepsy disease state, comprising:
receiving at least one autonomic index;
receiving at least one neurologic index;
first comparing the at least one autonomic index to at least a first reference value associated with the at least one autonomic index;
second comparing the at least one neurologic index to at least a second reference value associated with the at least one neurologic index;
assessing a state of an epilepsy disease of a patient based on an output of the first comparing and an output of the second comparing, wherein assessing comprises determining a change in at least one of a seizure severity value or an interseizure interval; and providing an output relating to the assessment, the output comprising at least one of disease stability, disease progression, disease regression, or a finding that the assessment could not determine a disease state.

2. The non-transitory computer readable program storage unit of claim 1, wherein the output comprises at least one of a magnitude of a change of a progression, a magnitude of a change of a regression, a rate of change of a progression, or a rate of change of a regression.

3. The non-transitory computer readable program storage unit of claim 1, wherein the at least one autonomic index comprises a cardiovascular parameter, a respiration parameter, a body temperature parameter, a skin resistance parameter, or two or more thereof; and
the at least one neurologic index comprises an attention aptitude parameter, a responsiveness parameter, a memory parameter, a kinetic parameter, a cognitive aptitude parameter, or two or more thereof.

4. The non-transitory computer readable program storage unit of claim 3, wherein the at least one autonomic index comprises at least one cardiovascular parameter selected from a heart rate parameter or a heart rate variability parameter, and the at least one neurologic index comprises at least one of a responsiveness parameter or a kinetic parameter selected from an electromyogram signal, an accelerometer signal, an inclinometer signal, or a parameter derived from one of the foregoing signals.

5. The non-transitory computer readable program storage unit of claim 1, wherein the method further comprises providing a warning signal to the patient, a physician, or a caregiver if said assessing indicates disease progression.

6. The non-transitory computer readable program storage unit of claim 5, wherein the warning signal is proportional to at least one of a magnitude of a change of a progression, a rate of change of a disease progression, or a correlation of the index value to life span.

7. The non-transitory computer readable program storage unit of claim 1, wherein the method further comprises assessing a state of at least one body system of a patient based on the comparing, wherein the body system is selected from an autonomic system, a neurological system, a psychiatric system, an endocrine system, or subsystems of the foregoing, and wherein the output comprises at least one of body system stability, body system improvement, body system decline, or a finding that a state of the body system cannot be determined.

8. The non-transitory computer readable program storage unit of claim 7, wherein a subsystem of the autonomic system is selected from a cardiovascular subsystem or a respiratory subsystem, and a subsystem of the neurologic system is a body kinetic subsystem.

9. The non-transitory computer readable program storage unit of claim 1, wherein the output comprises identifying one or more comorbidities associated with the disease.

10. The non-transitory computer readable program storage unit of claim 1, wherein the method further comprises forecasting a state of the disease, wherein the forecast comprises a disease stability, a disease progression, a disease regression, or a finding that no forecast can be made.

11. The non-transitory computer readable program storage unit of claim 10, wherein the forecast is of disease progression and the forecast comprises at least one of a risk of an increased magnitude of change of progression, a risk of an increased rate of change of progression, or a risk of emergence of one or more comorbidities associated with the disease.

12. The non-transitory computer readable program storage unit of claim 1, wherein the autonomic index comprises a weighted composite of a plurality of autonomic indices, the neurologic index comprises a weighted composite of a plurality of neurologic indices, or both.

13. The non-transitory computer readable program storage unit of claim 1, wherein at least one of the first reference value or the second reference value is based on the patient's index value history or on normative data.

14. The non-transitory computer readable program storage unit of claim 1, wherein the at least one autonomic index, the at least one neurologic index, or both comprises a measure of central tendency, a measure of dimensionality, a measure of fractality, a measure of stationarity, a measure of long-range dependency, a measure of clustering, a distribution of measures of central tendency, a distribution of measures of dimensionality, a distribution of measures of fractality, a distribution of measures of stationarity, a distribution of measures of long-range dependency, a distribution of measures of clustering, or two or more thereof.

15. The non-transitory computer readable program storage unit of claim 1, wherein the method further comprises assessing the patient's overall health.

16. The non-transitory computer readable program storage unit of claim 15, wherein the method further comprises using the assessment of the patient's overall health and an assessment of the patient's quality of life to assess the patient's well being.

17. A medical device system, comprising:
an autonomic index determination unit capable of determining at least one autonomic index;
a neurologic index determination unit capable of determining at least one neurologic index;
an index comparison unit capable of first comparing the at least one autonomic index with at least one first reference value and second comparing the at least one neurologic index with at least one second reference value;
an epilepsy disease state assessment unit capable of assessing a state of an epilepsy disease based on an output by the index comparison unit of the first comparing and an output by the index comparison unit of the second comparing, wherein assessing comprises determining a change in at least one of a seizure severity value or an interseizure interval; and
an output unit capable of providing an output relating to the assessment, wherein the output comprises at least one of disease stability, disease progression, disease regression, or a finding that the epilepsy disease state assessment unit could not determine a disease state.

18. The medical device system of claim 17, further comprising:
a warning unit adapted to provide a warning if the epilepsy disease state assessment unit yields an assessment of disease progression.

19. The medical device system of claim 17, wherein the autonomic index determination unit comprises at least one of:
a cardiovascular indication processing unit, a respiration indication processing unit,
a blood parameter indication processing unit,
a pupillary response indication processing unit,
a body temperature indication processing unit, or
a skin resistance indication processing unit; and
the neurologic index determination unit comprises at least one of:
an attention aptitude indication processing unit,
a responsiveness indication processing unit,
a memory indication processing unit,
a kinetic indication processing unit, or
a cognitive aptitude indication processing unit.

20. The medical device system of claim 17, further comprising:
   a forecast unit capable of forecasting a state of the disease, wherein the forecast comprises a disease stability, a disease progression, a disease regression, or a finding that no forecast can be made.

21. A non-transitory computer readable program storage unit encoded with instructions that, when executed by a computer, perform a method for assessing an epilepsy disease state, comprising:
   receiving at least one autonomic index;
   receiving at least one neurologic index;
   first comparing the at least one autonomic index to at least a first reference value associated with the at least one autonomic index, wherein the at least one autonomic index comprises at least one cardiovascular parameter selected from a heart rate parameter or a heart rate variability parameter;
   second comparing the at least one neurologic index to at least a second reference value associated with the at least one neurologic index, wherein the at least one neurologic index comprises at least one of a responsiveness parameter or a kinetic parameter selected from an electromyogram signal, an accelerometer signal, an inclinometer signal, or a parameter derived from one of the foregoing signals;
   assessing a state of an epilepsy disease of a patient based on an output of the first comparing and an output of the second comparing, wherein assessing comprises determining a change in at least one of a seizure severity value or an interseizure interval; and
   providing an output relating to the assessment, the output comprising at least one of disease stability, disease progression, disease regression, or a finding that the assessment could not determine a disease state.

22. The non-transitory computer readable program storage unit of claim 1, wherein the disease state is a non-acute disease state.

23. The medical device of claim 17, wherein the epilepsy disease state assessment unit is capable of assessing a non-acute state of the epilepsy disease.

24. The non-transitory computer readable program storage unit of claim 21, wherein said assessment comprises determining a change in a mean, a median, or a percentile of said seizure severity value or said interseizure interval.

* * * * *